(12) United States Patent
Altin et al.

(10) Patent No.: US 8,779,107 B2
(45) Date of Patent: Jul. 15, 2014

(54) COMPOSITION FOR TARGETING DENDRITIC CELLS

(75) Inventors: Joseph Altin, Acton (AU); Ines Atmosukarto, Acton (AU); Rudolf Maria De Wildt, Stevenage (GB); Christopher Parish, Acton (AU); Jason Price, Acton (AU)

(73) Assignees: Lipotek Pty Ltd, Acton (AU); Domantis Limited, Brentwood (GB)

( * ) Notice: Subject to any disclaimer, the term of this patent is extended or adjusted under 35 U.S.C. 154(b) by 265 days.

(21) Appl. No.: 13/125,332

(22) PCT Filed: Oct. 19, 2009

(86) PCT No.: PCT/EP2009/063656
§ 371 (c)(1),
(2), (4) Date: Apr. 21, 2011

(87) PCT Pub. No.: WO2010/046338
PCT Pub. Date: Apr. 29, 2010

(65) Prior Publication Data
US 2011/0212168 A1   Sep. 1, 2011

Related U.S. Application Data

(60) Provisional application No. 61/107,095, filed on Oct. 21, 2008.

(51) Int. Cl.
*C07K 16/00* (2006.01)
*C12P 21/08* (2006.01)
*A61K 39/395* (2006.01)
*A61K 9/127* (2006.01)

(52) U.S. Cl.
USPC ...................... 530/388.7; 424/153.1; 424/450

(58) Field of Classification Search
None
See application file for complete search history.

(56) References Cited

FOREIGN PATENT DOCUMENTS

WO   WO 2005018610 A1 *   3/2005
WO   WO2005035572 A2     4/2005

OTHER PUBLICATIONS

Holt et al., 2003, TRENDS in Biotech. vol. 21: 484-490.*
Park et al., 2001, INt. Immunol. vol. 13: 1293-1290.*
Demerest, et al., Current Opinion in Drug Discovery and Development, vol. 11, No. 5, pp. 675-687 (2008).
Engering, et al., Journal or Immunology, vol. 138, pp. 2118-2126 (2002).
Geijtenbeek, et al., Cell, vol. 100, pp. 575-585 (2000).
Geijtenbeek, et al., Annu. Rev. Immunol., vol. 22, pp. 33-54 (2004).
Hersey, et al, Journal of Clinical Oncology, vol. 20, No. 20, pp. 4181-4190 (2002).
Kretz-Rommel, et al., Journal of Immunotherapy, vol. 30, No. 7, pp. 715-726 (2007).
Mahnke, et al., Cancer Research, vol. 65, No. 15, pp. 7007-7012 (2005).
Soilleux, Clinical Science, vol. 104, pp. 437-446 (2003).
Tacken, et al., Blood, vol. 106, No. 4, pp. 1278-1285 (2005).
Tacken, et al., Immunobiology, vol. 211, No. 6-8, pp. 599-608 (2006).
Van Broekhoven, et al., Cancer Research, vol. 64, No. 12, pp. 4357-4365 (2004).

* cited by examiner

*Primary Examiner* — Amy Juedes
(74) *Attorney, Agent, or Firm* — Gordon & Rees LLP

(57) ABSTRACT

The present disclosure relates to a composition for targeting dendritic cells. In particular, the present disclosure relates to a composition comprising: a) one or more antigens; b) an anti-DC-SIGN immunoglobulin single variable domain; and c) a carrier which carries a) and b). The disclosure further relates to formulations, compositions and devices comprising such anti-DC-SIGN molecules and their use as a medicament and in the treatment of cancer, suitably melanoma.

17 Claims, 19 Drawing Sheets

DMS5000 sequence without the His-tag:

STEVQLLESGGGLVQPGGSLRLSCAASGFTFDRRAMGWVRQAPGKGLEWVSSIESDGTRTYYADSVKGRFTISRDNSKNTLYLQMNSLRAEDTAVYYCAKHPGSSYVFDYWGQGTLVTVSS (SEQ ID NO: 1)

with the His-Tag (underlined):

STEVQLLESGGGLVQPGGSLRLSCAASGFTFDRRAMGWVRQAPGKGLEWVSSIESDGTRTYYADSVKGRFTISRDNSKNTLYLQMNSLRAEDTAVYYCAKHPGSSYVFDYWGQGTLVTVSS<u>GHHGHHHGHHHGHH</u> (SEQ ID NO: 2)

DMS5000 without ST:

EVQLLESGGGLVQPGGSLRLSCAASGFTFDRRAMGWVRQAPGKGLEWVSSIESDGTRTYYADSVKGRFTISRDNSKNTLYLQMNSLRAEDTAVYYCAKHPGSSYVFDYWGQGTLVTVSS (SEQ ID NO: 3)

FIG. 12

TABLE 1 Composition and characteristics of the Lipovaxin-MM pre-formulation components

| Pre-mix Component | A | B | C | D |
|---|---|---|---|---|
| Name | MM200 vesicles | Liposome | IFN-gamma | DMS5000 |
| Trade name | N/A | N/A | IMUKIN (Boehringer Ingelheim) | N/A<br>Recombinant protein |
| Composition/ description or structure if applicable | MM200 cell-membrane fraction which form multilamellar vesicles when resuspended in Phosphate Buffered Saline (PBS) | 3NTA-DTDA | IFN-gamma cytokine | Anti-human DC-SIGN V-domain antibody (dAb) solubilised in Phosphate Buffered Saline (PBS) |

| | | | |
|---|---|---|---|
| applicable) | | POPC<br>$C_{42}H_{82}NO_8P$<br><br>$NiSO_4$:<br>$NiSO_4 \cdot 6H_2O$ | |
| Molecular Weight | N/A | 3NTA-DTDA: 1486.8418<br><br>POPC: 760.10<br><br>$NiSO_4$: 154.77 (anhy) | 16,465 Dalton monomers | 14,386 kDa |
| Description | Vesicles are membrane bound multilamellar structures of varying sizes that form spontaneously when the membrane fraction collected from MM200 | The liposomes are prepared from a mixture of sterilised lipid solutions formulated in PBS supplemented with nickel sulphate. | IMUKIN is a highly purified sterile solution consisting of non-covalent dimers of two identical 16,465 Dalton monomers, with a | |

FIG. 13 CONT'D

| | | |
|---|---|---|
| | cells that have been disrupted by sonication is resuspended in an aqueous solution. Production is conducted under aseptic conditions. | The sterile mixture is lyophilised and stored under vacuum at -20°C. | specific activity of 20 million IU/mg. Excipients include mannitol, sodium succinate, succinic acid, polysorbate 20 and water for injection |
| Solubility | Suspension | Suspension | Soluble in PBS | Soluble in PBS |

FIG. 13 CONT'D

SEQUENCE LISTING

<160> NUMBER OF SEQ ID NOS: 3

<210> SEQ ID NO 1
<211> LENGTH: 121
<212> TYPE: PRT
<213> ORGANISM: Artificial Sequence
<220> FEATURE:
<223> OTHER INFORMATION: Source: DMS5000 dAb amino acid sequence encoded by an Escherchia coli phage library.

<400> SEQUENCE: 1

```
Ser Thr Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Asp
            20                  25                  30

Arg Arg Ala Met Gly Trp Val Arg Gln Ala Pro Gly Lys Gly Leu Glu
        35                  40                  45
```

-continued

```
Trp Val Ser Ser Ile Glu Ser Asp Gly Thr Arg Thr Tyr Tyr Ala Asp
 50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Lys His Pro Gly Ser Ser Tyr Val Phe Asp Tyr Trp Gly
                100                 105                 110

Gln Gly Thr Leu Val Thr Val Ser Ser
            115                 120
```

<210> SEQ ID NO 2
<211> LENGTH: 136
<212> TYPE: PRT
<213> ORGANISM: Artificial Sequence
<220> FEATURE:
<223> OTHER INFORMATION: Source: DMS5000 dAb amino acid sequence encoded
     by an Escherchia coli phage display library which comprises a HIS
     tag.

<400> SEQUENCE: 2

```
Ser Thr Glu Val Gln Leu Leu Glu Ser Gly Gly Gly Leu Val Gln Pro
 1                   5                  10                  15

Gly Gly Ser Leu Arg Leu Ser Cys Ala Ala Ser Gly Phe Thr Phe Asp
                 20                  25                  30

Arg Arg Ala Met Gly Trp Val Arg Gln Ala Pro Gly Lys Gly Leu Glu
             35                  40                  45

Trp Val Ser Ser Ile Glu Ser Asp Gly Thr Arg Thr Tyr Tyr Ala Asp
 50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Lys His Pro Gly Ser Ser Tyr Val Phe Asp Tyr Trp Gly
                100                 105                 110

Gln Gly Thr Leu Val Thr Val Ser Ser Gly His His Gly His His Gly
            115                 120                 125

His His Gly His His Gly His His
        130                 135
```

<210> SEQ ID NO 3
<211> LENGTH: 119
<212> TYPE: PRT
<213> ORGANISM: Artificial Sequence
<220> FEATURE:
<223> OTHER INFORMATION: Source: DMS5000 dAb amino acid sequence encoded
     by an Escherchia coli phage display library which lacks the amino
     terminal "ST" amino acid residues.

<400> SEQUENCE: 3

```
Glu Val Gln Leu Leu Glu Ser Gly Gly Gly Leu Val Gln Pro Gly Gly
 1                   5                  10                  15

Ser Leu Arg Leu Ser Cys Ala Ala Ser Gly Phe Thr Phe Asp Arg Arg
                 20                  25                  30

Ala Met Gly Trp Val Arg Gln Ala Pro Gly Lys Gly Leu Glu Trp Val
             35                  40                  45

Ser Ser Ile Glu Ser Asp Gly Thr Arg Thr Tyr Tyr Ala Asp Ser Val
 50                  55                  60
```

```
Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
            85                  90                  95

Ala Lys His Pro Gly Ser Ser Tyr Val Phe Asp Tyr Trp Gly Gln Gly
            100             105                 110

Thr Leu Val Thr Val Ser Ser
            115
```

COMPOSITION FOR TARGETING DENDRITIC CELLS

This application is a 371 of International Application No. PCT/EP2009/063656, filed Oct. 19, 2009, which claims the benefit of U.S. Provisional Application No. 61/107,095, filed Oct. 21, 2008, which is incorporated herein in its entirety.

The present invention relates to a composition for targeting dendritic cells. In particular, the present invention relates to a composition for vaccination which comprises membrane vesicles comprising antigens and dendritic cell targeting molecules. Suitably the dendritic cell targeting molecules are molecules which bind to DC-SIGN. The invention further relates to uses, formulations, compositions and devices comprising such anti-DC-SIGN molecules.

BACKGROUND OF THE INVENTION

Malignant melanoma is responsible for 79% of skin cancer-related death, despite the fact that it accounts for only 4% of all skin cancers[1]. Australia and New Zealand have the highest rate of incidence and mortality for melanoma and its occurrence is reported to be on the rise [2].

Malignant melanoma arises from mutations in the melanin producing cells, melanocytes. Because melanocytes are found mostly in the epidermal layer of the skin, it is consequently the most common place for primary melanoma lesions [3]. Primary lesions can also occur at non-cutaneous sites where melanocytes are found, such as the oral mucosa, nasopharynx, paranasal sinuses, tracheobronchial tree, vulva, vagina, anus, urinary tract, central nervous system and eye [4]. A staging system is used to measure the extent and seriousness of the disease that is based on the examination of the primary tumour and the extent of the spread. Because no reliable blood markers have been identified for screening purposes, diagnosis relies on measurements obtained through physical examination and radiology techniques. These measurements are used to determine overall staging (Stage 0 to Stage IV) and patient prognosis. Early stages (0, I and II) show no spread of the primary tumour and have very good prognosis. These early stages are differentiated mainly based on depth of the invading tumour. When the primary tumour has metastasised to the lymph glands or surrounding tissue but not to a distant lymph node or other organ, the patient is diagnosed as stage III. When the melanoma has spread to a distant organ(s) or distant lymph gland(s), stage IV of the disease is diagnosed [5]. Since early stages of melanoma are generally symptomless, by the time a patient is diagnosed the cancer is generally at advanced stages (stages III or IV) and prognosis is consequently poor.

Early detection of cutaneous melanoma followed by an appropriate intervention has the most impact on the prognosis of patients with melanoma. When detected at stages 0-II, the recommended treatment is to remove the primary tumour, the skin and the flesh from around the primary tumour through surgery. When the condition is recognised early in its course and the primary tumour is surgically removed 97% of patients show no recurrence of the problem. Because incompletely excised tumours have a high rate of recurrence, and since patients with recurrent lesions have lower rates of long term cure, it is important to remove the entire tumour [6]. The depth of invasion of the tumor at the time of diagnosis most accurately predicts survival from melanoma: the survival rate associated with melanoma is inversely related to its depth at the time of diagnosis. When the primary melanoma has invaded more deeply, a sentinel node biopsy is conducted for more accurate staging of the disease and to assist in determining the need for additional treatment.

When later stages (III and IV) are diagnosed, the treatment options that exist for malignant melanoma are unsatisfactory, and long term survival of metastatic melanoma patients is a relatively rare event [7]. For stage III patients, the lymph node surrounding the node that tested positive to melanoma is generally removed. When patients are medically unfit for surgery or have unresectable disease because it is too extensive, radiotherapy may be used as an alternative to surgery. Post-operative radiotherapy is also considered in patients who have positive or close margins following surgery or where metastases to lymph nodes raise the risk of regional occurrence [8]. For stage IV melanoma, the standard treatment is chemotherapy using dacarbazine (DTIC) [9]. Other chemotherapy drugs such as lomustine and fotemustine are also approved for stage IV melanoma [10].

Two biological therapies have received FDA approval for use in the treatment of high risk melanoma patients: interferon alpha-2b and IL-2. Interferon alpha-2b is prescribed as adjuvant therapy to alter the natural history of the disease and in some studies shown to decrease recurrence rates of patients with fully resected high-risk malignant melanoma [11]. The treatment, however, requires repeated administration over a 52 week period which is associated with significant toxicities and considerable cost [12]. IL-2 is an immunotherapeutic agent used for patients with metastatic melanoma and is associated with a low but consistent rate of overall response of ~13-17% (7-% partial response and 6-8% complete response) [13, 14].

Melanoma is an immunogenic cancer. Large numbers of tumour infiltrating lymphocytes are often found naturally in melanoma patients, and many studies have reported that melanoma cells express antigens that can induce melanoma-specific T cell and antibody responses [15]. This has led to the design of various melanoma vaccine strategies, some of which are composed of whole cells, cell lysates, proteins and others of specific peptides. Dendritic cell-based vaccines that use ex vivo antigen-loaded DCs have also been tested with the aim of enhancing the patient's immune response to the tumour. However, despite over 15 years of studies none have yet been approved for use outside of a clinical trial [16].

Accordingly, there remains a need for an effective melanoma treatment.

SUMMARY OF THE INVENTION

In one aspect, the present invention provides a composition comprising:
  a) one or more antigens;
  b) an anti-DC-SIGN immunoglobulin single variable domain; and
  c) a carrier which carries a) and b).

In one embodiment, the composition further comprises d) an immunomodulatory factor. Suitable immunomodulatory factors are described, for example, in WO 2005/018610. Suitable immunomodulatory factors may also be described as "danger signals".

In one embodiment, one or more antigens are derived from membrane vesicles (MVs). Suitably, the membrane vesicles comprise one or more membrane-associated antigens, suitably, tumour antigens, including the melanoma differentiation antigens tyrosinase, gp100 and MART-1, or the cancer testis antigens MAGE-A3, MAGE A-10, BAGS, GAGE and XAGE.

In another embodiment, the one or more antigens may be derived from any polypeptide for which presentation on a dendritic cell may be desirable.

In one embodiment, the membrane vesicles are derived from tumour cells, preferably melanoma cells. A number of melanoma cell lines are available. In one embodiment, melanoma cells derived from the melanoma cell line MM200 are used. In another embodiment, the melanoma cells may be obtained from a patient. In one embodiment, the patient is a patient with malignant melanoma. In another embodiment, the tumour cells may be a cell line or patient cells derived from any form of cancer including, for example, bladder, breast, lung (including NSCLC), liver, seminomas and/or head and neck cancer.

In another embodiment, the anti-DC-SIGN immunoglobulin single variable domain is a single domain antibody (dAb), suitably a heavy chain dAb fragment such as a $V_H$ dAb fragment. In another embodiment, the anti-DC-SIGN immunoglobulin single variable domain is a light chain dAb fragment such as a $V_L$ dAb fragment. In one embodiment, the anti-DC-SIGN immunoglobulin single variable domain comprises the specific single domain antibody, identified herein as DMS5000, comprising an amino acid sequence as set out in SEQ ID NO: 1 of FIG. 12. In another embodiment, the anti-DC-SIGN immunoglobulin single variable domain is DMS5000 having an amino acid sequence as set out in SEQ ID NO: 1 of FIG. 12. In another embodiment, the anti-DC-SIGN immunoglobulin single variable domain comprises an amino acid as set out in SEQ ID NO: 3. In a further embodiment, the anti-DC-SIGN immunoglobulin single variable domain is one which has the same binding specificity as the anti-DC-SIGN immunoglobulin single variable domain having an amino acid sequence as set out in SEQ ID NO: 1 or SEQ ID NO: 3.

In another embodiment, the anti-DC-SIGN immunoglobulin single variable domain is one which has the same CDR sequences as the amino acid sequence set out in SEQ ID NO: 1 or 3.

The anti-DC-SIGN immunoglobulin single variable domain may further comprise a polyhistidine C-terminal tail. For example, the anti-DC-SIGN immunoglobulin single variable domain may comprise the amino acid sequence as set out in SEQ ID NO: 2 of FIG. 12. This polyhistidine C-terminal tail enables the anti-DC-SIGN immunoglobulin single variable domain to be tethered via the tail to the membrane vesicles using the chelator lipid 3NTA-DTDA.

Suitable carriers include any suitable delivery method such as biodegradable microcapsules or immuno-stimulating complexes (ISCOMs), cochleates, liposomes, genetically engineered attenuated live vectors such as viruses or bacteria, and recombinant (chimeric) virus-like particles, e.g., bluetongue. Other carrier systems in humans may include enteric release capsules protecting the antigen from the acidic environment of the stomach and polylactide-glycolide microspheres. Suitable diluents are 0.2 N NaHCO3 and/or saline.

In one embodiment, the carrier is a liposome. Suitably, the liposome comprises liposomal constituents. Such liposomal constituents enable the formation of liposomes. Suitable liposomal constituents are described, for example, in WO 2005/018610. Accordingly, in another embodiment, the liposomal constituents comprise the chelator lipid 3(nitrilotriacetic acid)-ditetradecylamine (3NTA-DTDA). In a further embodiment, the liposomal constituents also comprise nickel, preferably in the form of nickel sulphate (NiSO$_4$). NiSO$_4$ facilitates the interaction of the polyhistidine C-terminal tail with the chelator lipid 3NTA-DTDA.

In another embodiment, the liposomal constituents comprise the lipid α-palmitoyl-β-oleoyl-phosphatidylcholine (POPC)).

In one embodiment, the liposomal constituents may incorporate a hydrophilic polymer such as polyethylene glycol (PEG) in order to prolong presence of the liposomes in the circulation in vivo.

In another embodiment, the immunomodulatory factor is a cytokine which stimulates dendritic cells (DC). Suitably, the immunomodulatory factor is the cytokine interferon gamma (IFN-gamma). Other immunomodulatory factors include interleukin-2, interleukin-4, interleukin-10, interleukin-12 and transforming growth factor-β.

In one embodiment, the composition is a vaccine composition. In one embodiment, the vaccine composition is "Lipovaxin-MM" as described herein.

In another embodiment, the composition further comprises a pharmaceutically acceptable carrier. Suitably, the composition is prepared for administration intravenously.

In another aspect, the invention provides a method for making a composition in accordance with the invention comprising:
  i) preparing membrane vesicles;
  ii) preparing the liposomal constituent;
  iii) combining the membrane vesicles and the liposomal constituent with the immunomodulatory factor;
  iv) adding the anti-DC-SIGN immunoglobulin single variable domain.

In one embodiment, such steps for a method can be performed in any order.

In one embodiment, the preparation of membrane vesicles is by propagating tumour cells, sonicating and preparing membrane pellets by centrifugation and resuspension in PBS. In another embodiment, the liposomal constituent is prepared by mixing POPC and Ni-3NTA-DTDA. In a further embodiment, the method further comprises supplementing with nickel.

In another aspect, there is provided a composition in accordance with the invention for use as a medicament. In one aspect the composition in accordance with the invention is for use in the treatment of cancer. Suitably, the cancer is melanoma.

In another embodiment, the composition is for intravenous administration.

In another aspect, there is provided a method for treating a tumour in a subject comprising administering a composition in accordance with the invention.

BRIEF DESCRIPTION OF THE DRAWINGS

FIG. 2 shows by FACS analysis that increasing the number of targeting molecules on the surface of Lipovaxin-MM did not increase the targeting of the vaccine.

CD64 upregulation was measured by flow cytometry using an anti-CD64 mAb. The results are shown as mean±standard error.

Figure 7:
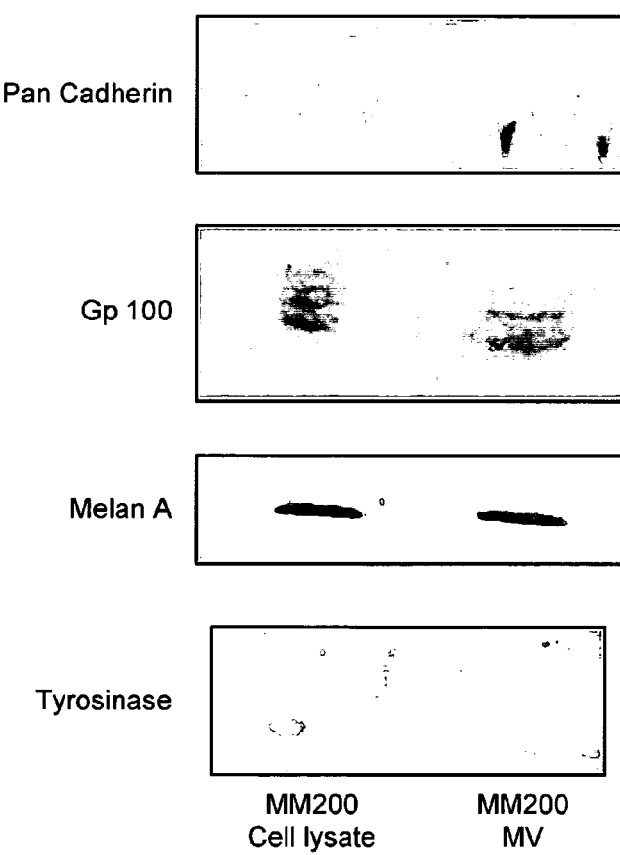

FIG. 7 Western Blot analysis of MM200 Membrane Vesicles. Cell lysates were prepared by sonication; MVs were prepared according to the standard operating procedures as described herein. The protein content of the samples was measured then samples were boiled with sample buffer, loaded onto precast NuSep gels (4-20%) and subjected to SDS-PAGE. Proteins were transferred onto nitrocellulose membranes and blocked overnight. Membranes were probed with primary antibody, washed and incubated with alkaline phosphatase conjugated secondary antibody. Bands were visualised using Promega's Western Blue stabilised substrate. Pan cadherin, Melan A and gp100 were visualised in both cell lysates (left) and MVs (right) prepared from MM200 cells.

Figure 8:
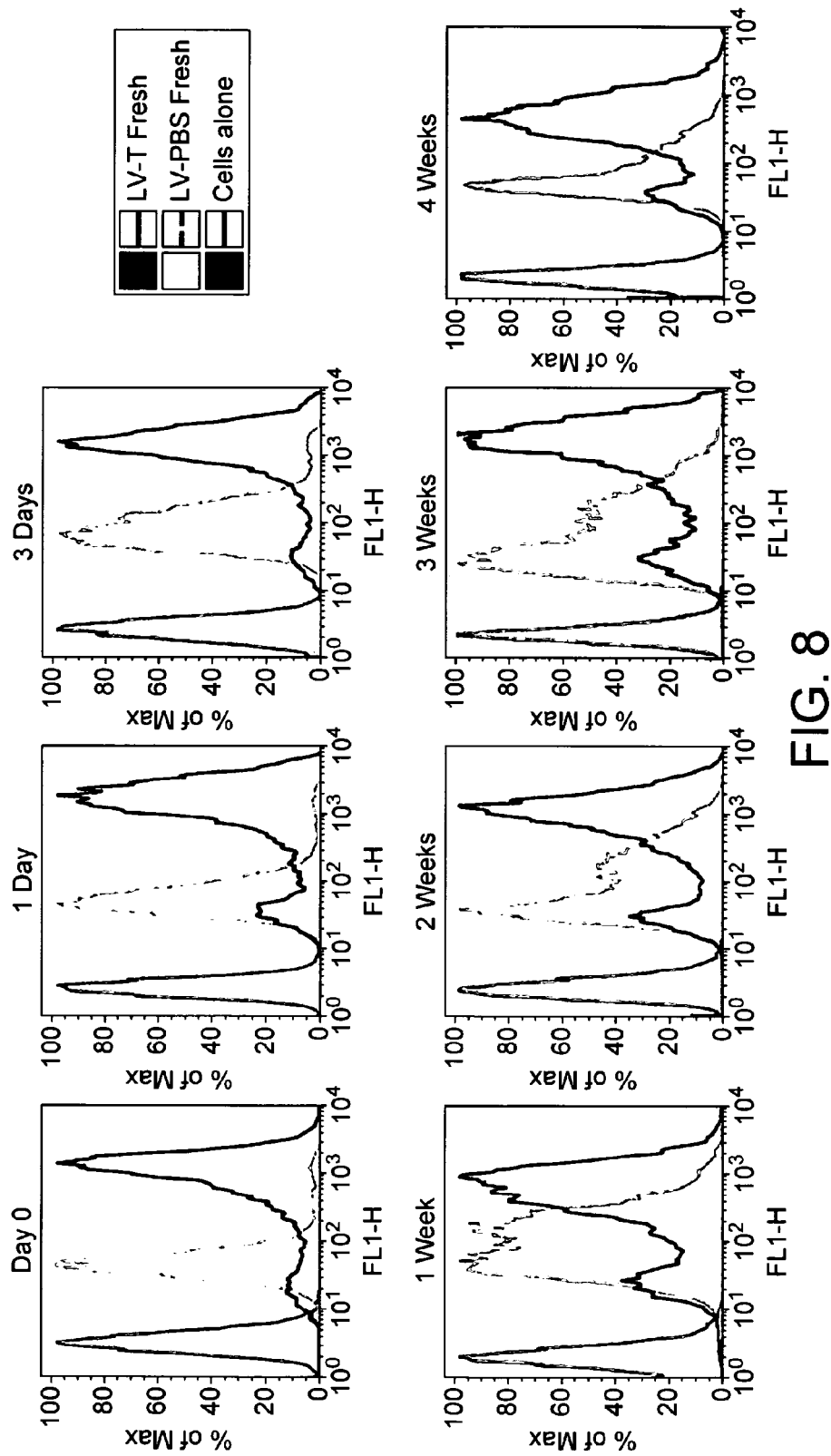

FIG. 8 Stability of Lipovaxin stored at 4° C.: Effect on binding of Lipovaxin-MM (LV-MM) to DC-SIGN in vitro. LV-MM was stored at 4° C. and binding assays using THP-1/DC-SIGN cells were performed on aliquots taken at various time points. LV-MM was fluorescinated with BODIPY-500-510-C dye. After storage for 4 weeks at 4° C., LV-MM was stable with respect to binding to DC-SIGN on THP-1/DC-SIGN cells.

Figure 9:
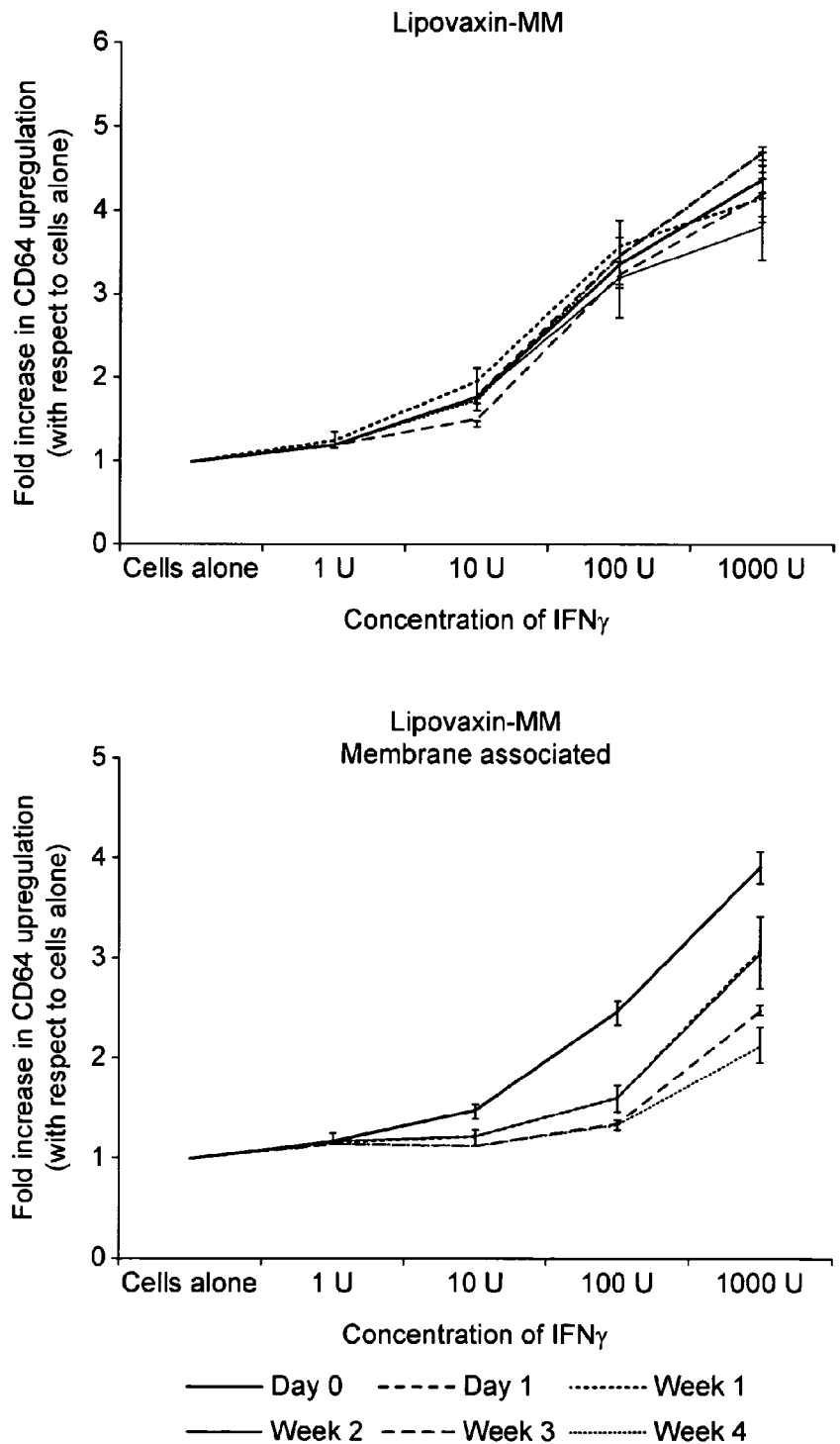

FIG. 9 Stability of Lipovaxin (LV-MM) stored at 4° C.: Effect on IFN-gamma Activity. IFN-gamma activity in fresh LV-MM and LV-MM stored at 4° C. was measured based on the expression of CD64 on THP-1/DCSIGN cells. The graph on the left represents whole LV-MM while that on the right represents LV-MM with non-membrane associated IFN-gamma removed by centrifugation. Cells were incubated for 48 hours at 37° C. with different concentrations of LV-MM. CD64 upregulation was measured by flow cytometry using an anti-CD64 mAb. The results are shown as mean±Standard error. After storage at 4° C., IFN-gamma in LV-MM was stable for up to 4 weeks. However, a reduction in the membrane bound IFN-gamma in LV-MM indicates that IFN-gamma becomes disassociated from the membrane over time.

Figure 10:
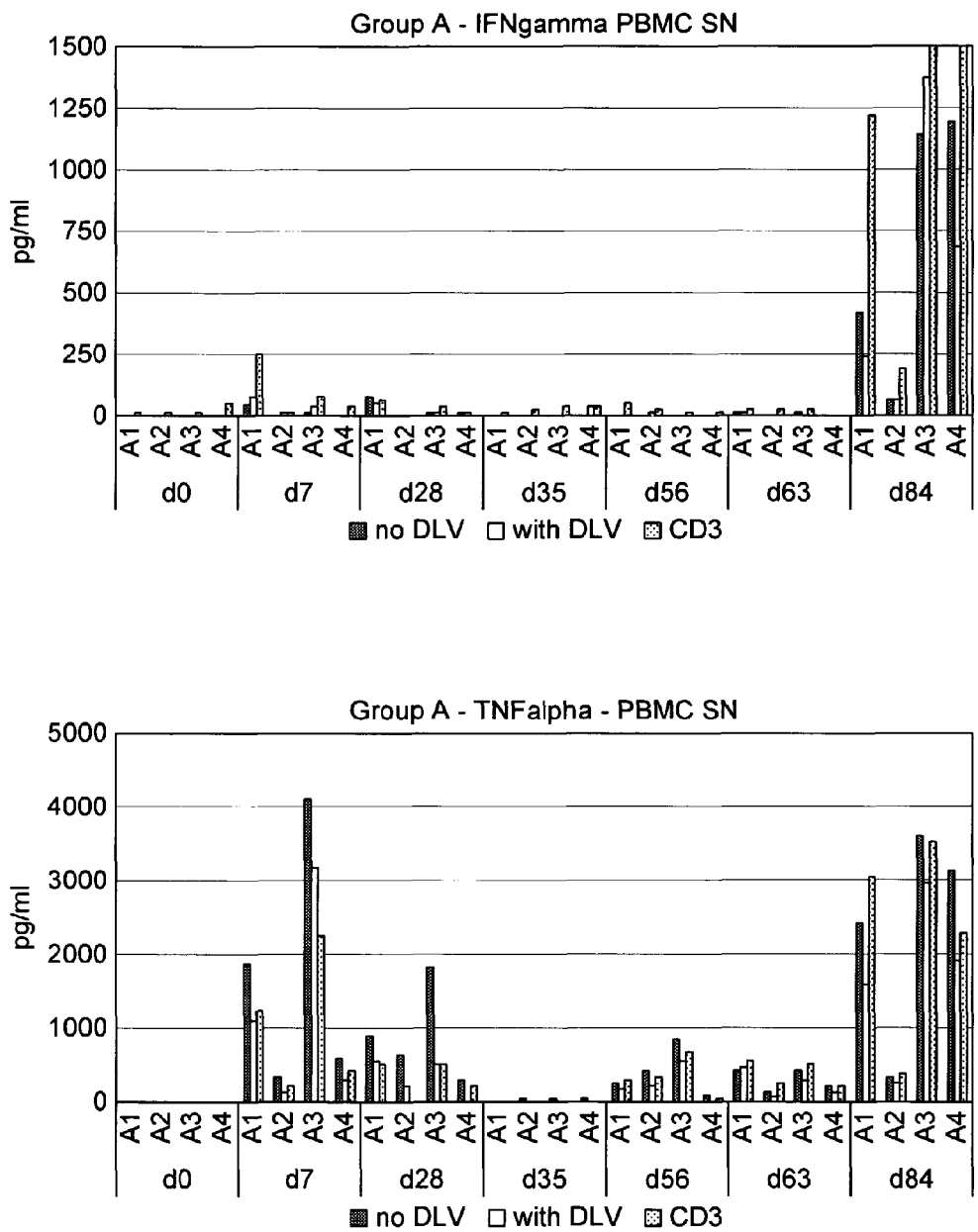
Figure 10:
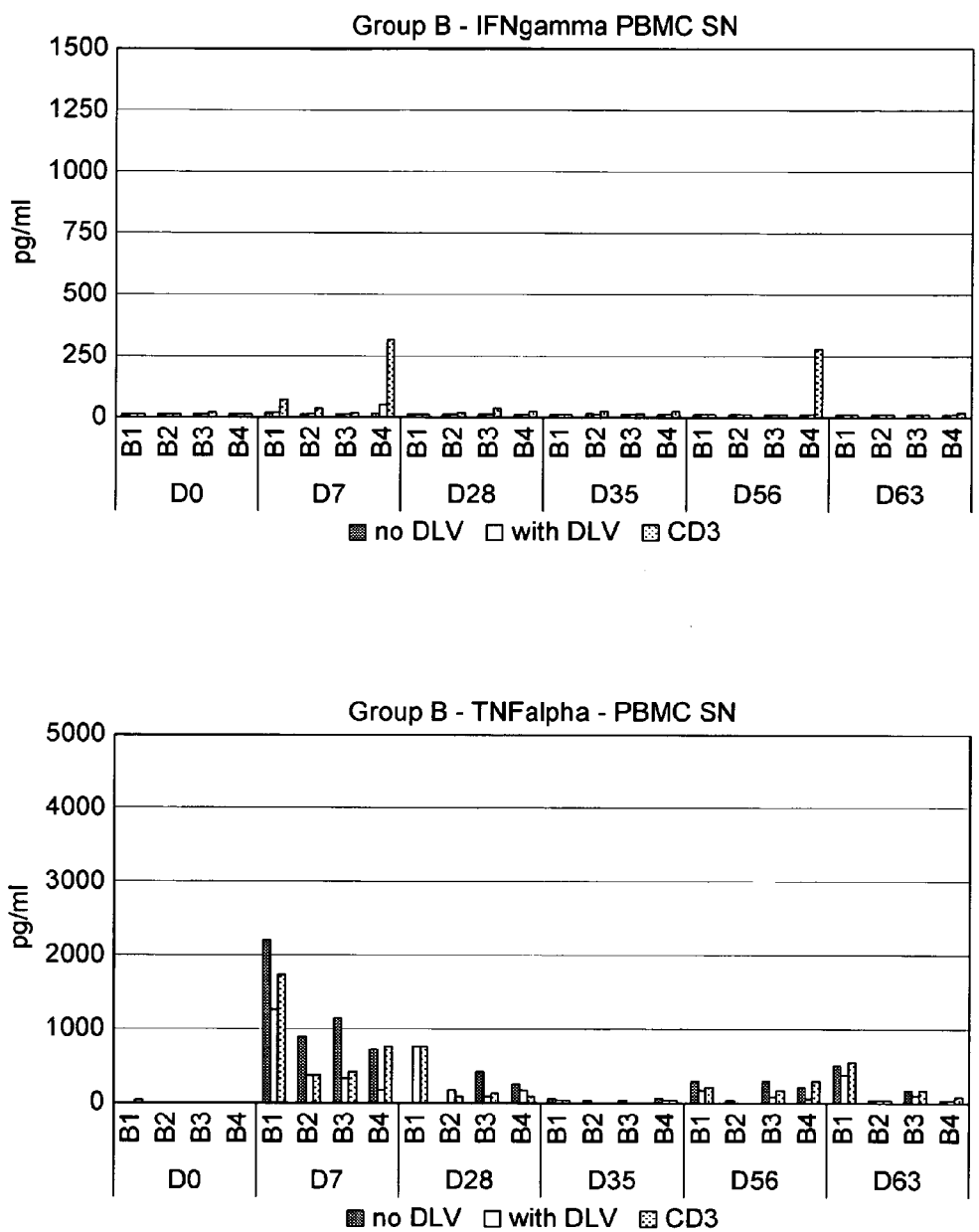

FIG. 10 IFN-gamma and TNF-alpha secretion by cultured PBMCs from macaques vaccinated with Lipovaxin-MM. Two groups (A and B) of 4 macaques were vaccinated with Lipovaxin-MM according to the schedule outlined below. Blood was taken at various times during the vaccination schedule and peripheral blood mononuclear cells (PBMCs) isolated and cultured for 48 hours with 'dummy' Lipovaxin-MM (lacking IFN-gamma) (with DLV), anti-CD3 mAb (CD3), or no stimulus (no DLV). Culture supernatants were collected and analysed for IFN-gamma and TNF-alpha production using the BD CBA Non-Human Primate Th1/Th2 Cytokine Kit. SN=supernatant.

Figure 11:
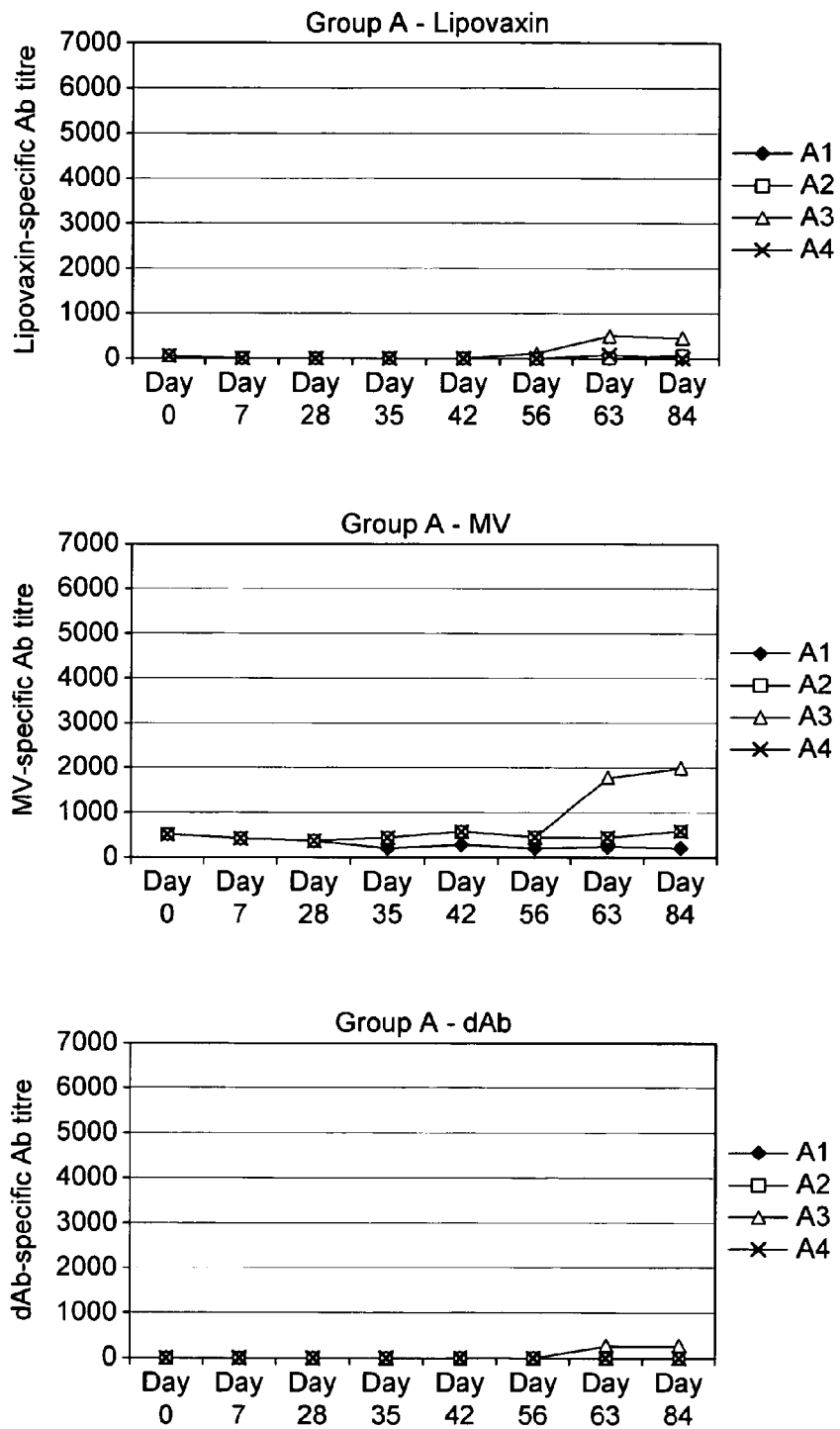
Figure 11:
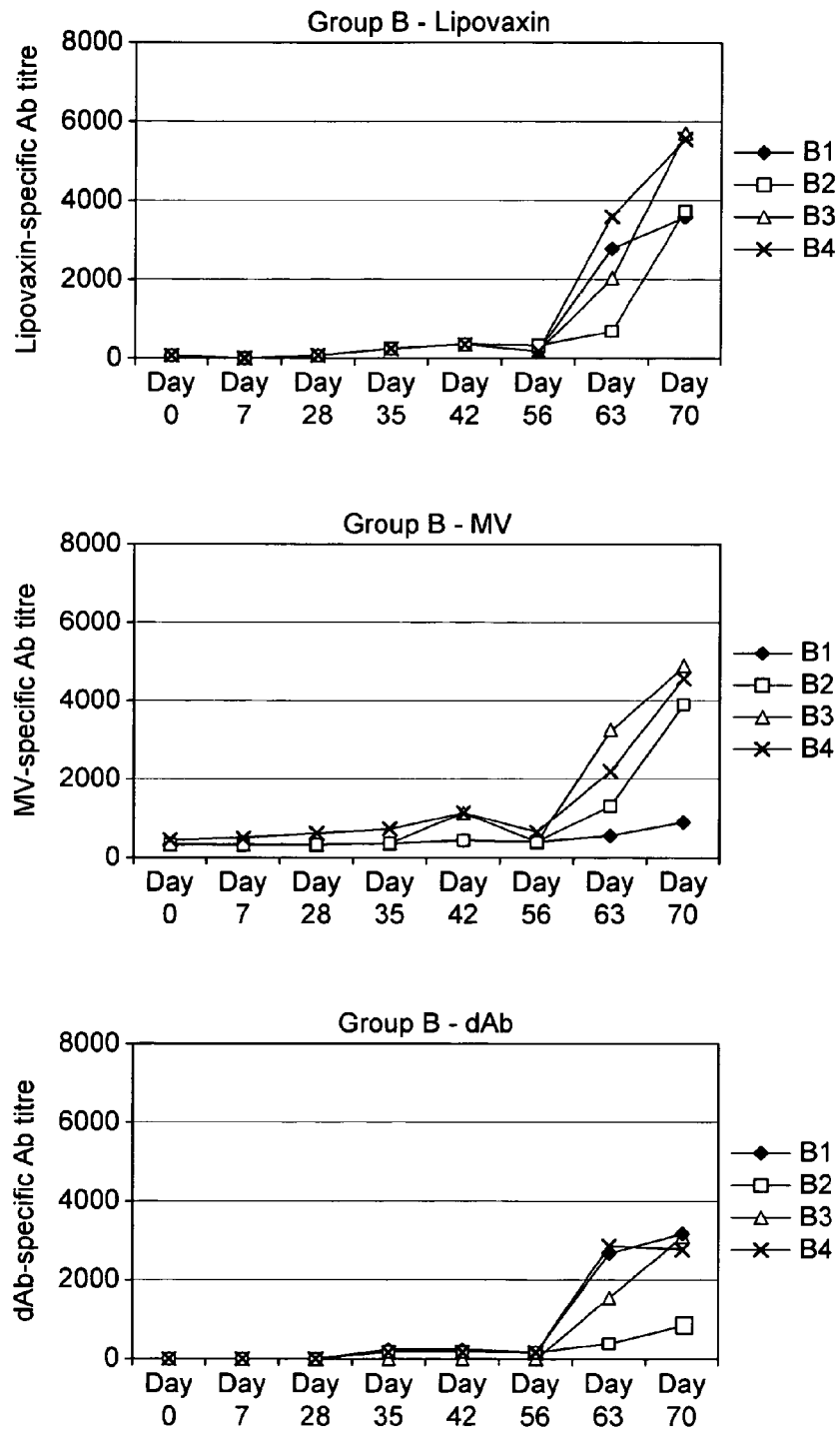

FIG. 11 Antibody production in macaques vaccinated with Lipovaxin-MM. Two groups (A and B) of 4 macaques were vaccinated with Lipovaxin-MM according to the schedule outlined below. Blood was taken at various times during the vaccination schedule and enzyme-linked immunosorbent assays performed to measure the production of antibodies specific to whole Lipovaxin-MM (Lipovaxin), the MM200 membrane vesicle component of Lipovaxin-MM (MV), and the domain antibody DMS5000 (dAb).

FIG. 12. DMS5000 amino acid sequences.

Figure 13:
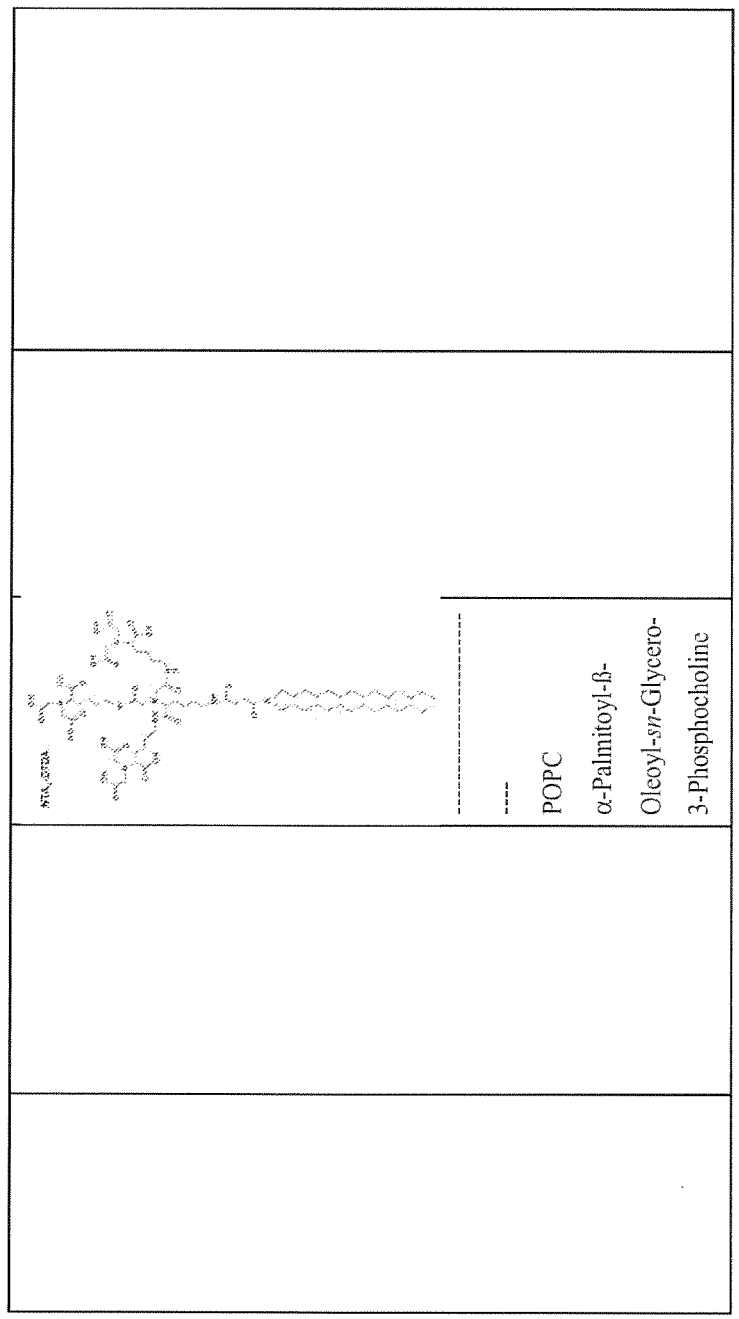
Figure 13:

FIG. 13. Table 1 Composition and characteristics of the Lipovaxin-MM pre-formulation components.

DETAILED DESCRIPTION OF THE INVENTION

Within this specification the invention has been described, with reference to embodiments, in a way which enables a clear and concise specification to be written. It is intended and should be appreciated that embodiments may be variously combined or separated without parting from the invention.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) $4^{th}$ Ed, John Wiley & Sons, Inc. which are incorporated herein by reference) and chemical methods.

Antigens for use in the compositions of the present invention include tumour antigens. Suitably, such antigens may include any antigens that are differentially expressed on tumour cells as compared to non-tumour cells derived from the same tissue. Differential expression may include, for example, up-regulation, alternatively spliced forms and so forth. Tumour antigens include the so-called cancer/testis antigens. These are antigens/proteins that are generally not expressed in normal tissues/cells other than the testes. However, these antigens are thought to be expressed specifically in certain cancers/tumors such as bladder, breast, lung particularly non-small cell lung cancer (NSCLC), liver, seminomas, melanoma, and/or head and neck cancers and advantageously are capable of being recognised by cytotoxic T-cells. More than 50 cancer/testis antigens have been described so far and, for many of them, specific epitopes recognized by T lymphocytes have been identified. In one embodiment of the invention, said one or more antigens may be any cancer/testis antigen.

A well characterised cancer/testis antigen family is the MAGE family, which includes 12 closely related genes, MAGE 1, MAGE 2, MAGE 3, MAGE 4, MAGE 5, MAGE 6, MAGE 7, MAGE 8, MAGE , MAGE 10, MAGE 11, MAGE 12, located on chromosome X and sharing with each other 64 to 85% homology in their coding sequence (De Plaen, Immunogenetics 1994, 40: 5 (360-369)). These are sometimes known as MAGE A1, MAGE A2, MAGE A3, MAGE A4, MAGE A5, MAGE A6, MAGE A7, MAGE A8, MAGE A9, MAGE A 10, MAGE Al 1, MAGE A 12 (The MAGE A family). Two other groups of proteins are also part of the MAGE family although more distantly related. These are the MAGE B and MAGE C group. The MAGE B family includes MAGE B1 (also known as MAGE Xp1, and DAM 10), MAGE B2 (also known as MAGE Xp2 and DAM 6) MAGE B3 and MAGE B4—the Mage C family currently includes MAGE C 1 and MAGE C2.

In one embodiment, antigens for use in the composition of the present invention are melanoma antigens. Suitable melanoma antigens are those that are recognized by T cells including the cancer/testis antigens such as MAGE-1 and MAGE-3. These antigens are also produced in other tumors. For example, MAGE-3 is found in small cell lung cell carcinoma (SCLC), non-small cell lung cell carcinoma (non-SCLC), squamous cell carcinoma of the head and neck (SCCHN), colon cancer, and breast cancer. MAGE-1 also is produced in breast cancer, glioblastoma, neuroblastoma, SCLC, and medullary cancer of the thyroid. Other melanoma antigens include melanocyte lineage-specific differentiation antigens including MART-1/Melan-A, tyrosinase, GP75, and GP100. Other suitable antigens include tyrosinase, BAGE, GAGE-1, 2, GnT-V, p15. In addition, tumor-specific mutated antigens such as b-catenin, MUM-1 and CDK4 are included.

Dendritic cell-specific ICAM-3 grabbing non-integrin (DC-SIGN or CD209) is a type II membrane protein that is mannose specific calcium dependent (C-type) lectin. DC-SIGN mediates interactions between dendritic cells (DCs) and T cells and is described, for example, by Soilleux, Clinical Science (2003), 104, 437-446 with sequence data given in NM_021155 (mRNA) and NP_066978 (protein).

Suitably, the anti-DC-SIGN immunoglobulin single variable domain of the invention can be presented in any antibody format.

As used herein an antibody refers to IgG, IgM, IgA, IgD or IgE or a fragment (such as a Fab, F(ab')$_2$, Fv, disulphide linked Fv, scFv, closed conformation multispecific antibody, disulphide-linked scFv, diabody) whether derived from any species naturally producing an antibody, or created by recombinant DNA technology; whether isolated from serum, B-cells, hybridomas, transfectomas, yeast or bacteria.

As used herein, "antibody format" refers to any suitable polypeptide structure in which one or more antibody variable domains can be incorporated so as to confer binding specificity for antigen on the structure. A variety of suitable antibody formats are known in the art, such as, chimeric antibodies, humanized antibodies, human antibodies, single chain antibodies, bispecific antibodies, antibody heavy chains, antibody light chains, homodimers and heterodimers of antibody heavy chains and/or light chains, antigen-binding fragments of any of the foregoing (e.g., a Fv fragment (e.g., single chain Fv (scFv), a disulfide bonded Fv), a Fab fragment, a Fab' fragment, a F(ab')$_2$ fragment), a single antibody variable domain (e.g., a dAb, $V_H$, $V_{HH}$, $V_L$), and modified versions of any of the foregoing (e.g., modified by the covalent attachment of polyethylene glycol or other suitable polymer or a humanized $V_{HH}$).

The phrase "immunoglobulin single variable domain" refers to an antibody variable domain ($V_H$, $V_{HH}$, $V_L$) that specifically binds an antigen or epitope independently of other V regions or domains. An immunoglobulin single variable domain can be present in a format (e.g., homo- or heteromultimer) with other variable regions or variable domains where the other regions or domains are not required for antigen binding by the single immunoglobulin variable domain (i.e., where the immunoglobulin single variable domain binds antigen independently of the additional variable domains). A "domain antibody" or "dAb" is the same as an "immunoglobulin single variable domain" as the term is used herein. A "single immunoglobulin variable domain" is the same as an "immunoglobulin single variable domain" as the term is used herein. A "single antibody variable domain" or an "antibody single variable domain" is the same as an "immunoglobulin single variable domain" as the term is used herein. An immunoglobulin single variable domain is in one embodiment a human antibody variable domain, but also includes single antibody variable domains from other species such as rodent (for example, as disclosed in WO 00/29004, the contents of which are incorporated herein by reference in their entirety), nurse shark and Camelid $V_{HH}$ dAbs. Camelid $V_{HH}$ are immunoglobulin single variable domain polypeptides that are derived from species including camel, llama, alpaca, dromedary, and guanaco, which produce heavy chain antibodies naturally devoid of light chains. The $V_{HH}$ may be humanized.

A "domain" is a folded protein structure which has tertiary structure independent of the rest of the protein. Generally, domains are responsible for discrete functional properties of proteins, and in many cases may be added, removed or transferred to other proteins without loss of function of the remainder of the protein and/or of the domain. A "single antibody variable domain" is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain.

Specific binding of an antigen-binding protein (binding specificity) such as a dAb to an antigen or epitope can be determined by any suitable assay, including, for example, Scatchard analysis and/or competitive binding assays, such as radioimmunoassays (RIA), enzyme immunoassays such as ELISA and sandwich competition assays, and the different variants thereof.

Complementarity Determining Regions (CDRs) and framework regions are those regions of an immunoglobulin variable domain. In particular there are regions of the sequence of a single antibody variable domain which display particular variability i.e. the CDR (complementarity determining region) sequences. The CDRs are at defined positions within the sequence of the antibody variable domain. A number of systems for defining the CDR regions of a sequence will be familiar to those skilled in the art. In one embodiment, the CDR sequences of the present invention are as defined in the Kabat database of Sequences of Proteins of Immunological Interest (Kabat E. A., Wu, T. T., Perry, H., Gottesman, K. and Foeller, C. (1991) *Sequences of Proteins of Immunological Interest*, Fifth Edition. NIH Publication No. 91-3242) which gives a standard numbering scheme for numbering the residues in an antibody in a consistent manner. The immunoglobulin single variable domains (dAbs) described herein contain complementarity determining regions (CDR1, CDR2 and CDR3).

The amino acid sequences of the CDRs (CDR1, CDR2, CDR3) of the $V_H$ (CDRH1 etc.) and $V_L$ (CDRL1 etc.) ($V_K$) dAbs described herein will be readily apparent to the person of skill in the art based on the well known Kabat amino acid numbering system and definition of the CDRs. According to the Kabat numbering system, the most commonly used method based on sequence variability, heavy chain CDR-H3 have varying lengths, insertions are numbered between residue H100 and H101 with letters up to K (i.e. H100, H100A . . . H100K, H101). CDRs can alternatively be determined using the system of Chothia (based on location of the structural loop regions) (Chothia et al., (1989) Conformations of immunoglobulin hypervariable regions; Nature 342 (6252), p877- 883), according to AbM (compromise between Kabat and Chothia) or according to the Contact method (based on crystal structures and prediction of contact residues with antigen) as follows. See http://www.bioinf.org.uk/abs/ for suitable methods for determining CDRs.

Once each residue has been numbered, one can then apply the following CDR definitions:

Kabat:

CDR H1: 31-35/35A/35B
CDR H2: 50-65
CDR H3: 95-102
CDR L1: 24-34
CDR L2: 50-56
CDR L3: 89-97

Chothia:

CDR H1: 26-32
CDR H2: 52-56
CDR H3: 95-102
CDR L1: 24-34
CDR L2: 50-56
CDR L3: 89-97

AbM:

| (using Kabat numbering): | (using Chothia numbering): |
|---|---|
| CDR H1: 26-35/35A/35B | 26-35 |
| CDR H2: 50-58 | — |
| CDR H3: 95-102 | — |
| CDR L1: 24-34 | — |
| CDR L2: 50-56 | — |
| CDR L3: 89-97 | — |

Contact

| (using Kabat numbering): | (using Chothia numbering): |
|---|---|
| CDR H1: 30-35/35A/35B | 30-35 |
| CDR H2: 47-58 | — |
| CDR H3: 93-101 | — |
| CDR L1: 30-36 | — |
| CDR L2: 46-55 | — |
| CDR L3: 89-96 | — |

("—" means the same numbering as Kabat)

The present invention provides a vaccine or pharmaceutical composition which, optionally further includes a pharmaceutically acceptable carrier.

Generally, the composition of the invention will be utilised in purified form together with pharmacologically appropriate carriers. Typically, these carriers include aqueous or alcoholic/aqueous solutions, emulsions or suspensions, any including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) *Remington's Pharmaceutical Sciences,* 16th Edition). A variety of suitable formulations can be used, including extended release formulations.

The composition of the present invention may be used as separately administered compositions or in conjunction with other agents. Pharmaceutical compositions can include "cocktails" of various cytotoxic or other agents in conjunction with the composition of the present invention, or even combinations of compositions having different specificities, such as compositions comprising ligands selected using different target antigens or epitopes, or compositions comprising different immunomodulatory factors, whether or not they are pooled prior to administration.

The route of administration of pharmaceutical compositions according to the invention may be any of those commonly known to those of ordinary skill in the art. For therapy, including without limitation immunotherapy, the selected compositions of the invention can be administered to any patient in accordance with standard techniques.

The administration can be by any appropriate mode, including parenterally, intravenously, intramuscularly, intraperitoneally, transdermally, via the pulmonary route, or also, appropriately, by direct infusion with a catheter. The dosage and frequency of administration will depend on the age, sex and condition of the patient, concurrent administration of other drugs, counter indications and other parameters to be taken into account by the clinician. Administration can be local (e.g., local delivery to the lung by pulmonary administration, e.g., intranasal administration) or systemic as indicated.

The anti-DC-SIGN immunoglobulin single variable domains for use in the composition of the present invention can be lyophilised for storage and reconstituted in a suitable carrier prior to use. This technique has been shown to be effective with conventional immunoglobulins and art-known lyophilisation and reconstitution techniques can be employed. It will be appreciated by those skilled in the art that lyophilisation and reconstitution can lead to varying degrees of antibody activity loss (e.g. with conventional immunoglobulins, IgM antibodies tend to have greater activity loss than IgG antibodies) and that use levels may have to be adjusted upward to compensate.

The composition of the present invention or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system. For prophylactic applications, compositions containing the present composition or cocktails thereof may also be administered in similar or slightly lower dosages, to prevent, inhibit or delay onset of disease (e.g., to sustain remission or quiescence, or to prevent acute phase). The skilled clinician will be able to determine the appropriate dosing interval to treat, suppress or prevent disease.

Treatment or therapy performed using the compositions described herein is considered "effective" if one or more symptoms are reduced (e.g., by at least 10% or at least one point on a clinical assessment scale), relative to such symptoms present before treatment, or relative to such symptoms in an individual (human or model animal) not treated with such composition or other suitable control. Symptoms will obviously vary depending upon the disease or disorder targeted, but can be measured by an ordinarily skilled clinician or technician. Such symptoms can be measured, for example, by monitoring the level of one or more biochemical indicators of the disease or disorder (e.g., levels of an enzyme or metabolite correlated with the disease, affected cell numbers, etc.), by monitoring physical manifestations (e.g., inflammation, tumor size, etc.), or by an accepted clinical assessment scale. A sustained (e.g., one day or more, or longer) reduction in disease or disorder symptoms by at least 10% or by one or more points on a given clinical scale is indicative of "effective" treatment. Similarly, prophylaxis performed using a composition as described herein is "effective" if the onset or severity of one or more symptoms is delayed, reduced or abolished relative to such symptoms in a similar individual (human or animal model) not treated with the composition.

A composition according to the present invention may be utilised in prophylactic and therapeutic settings to aid in the alteration, inactivation, killing or removal of a select target cell population in a mammal.

The composition can be administered and or formulated together with one or more additional therapeutic or active agents. When a composition is administered with an additional therapeutic agent, the composition can be administered before, simultaneously with or subsequent to administration of the additional agent. Generally, the composition and additional agent are administered in a manner that provides an overlap of therapeutic effect.

As used herein, the term "dose" refers to the quantity of composition administered to a subject all at one time (unit dose), or in two or more administrations over a defined time interval. For example, dose can refer to the quantity of composition administered to a subject over the course of one day (24 hours) (daily dose), two days, one week, two weeks, three weeks or one or more months (e.g., by a single administration, or by two or more administrations). The interval between doses can be any desired amount of time.

Suitably the composition is for administration to a patient suffering from cancer and, in particular, melanoma, and for treatment of that patient.

As used herein, the terms "treating" or "treatment" refer to a prevention of the onset of disease or a symptom of disease, inhibition of the progression of a disease or a symptom of a disease, or the reversal of disease or a disease symptom.

The search for effective melanoma vaccines/immunotherapies is based on the principle that the immune system can be manipulated de novo by therapeutic vaccination in order to boost endogenous immune function against the cancer, to break immune tolerance to the cancer, and to stimulate the destruction of tumour cells [17]. It is now recognised that DCs play a central role in the initiation of the T cell-mediated adaptive immune responses which are important for the destruction of tumours [18]. DCs are unique in their ability to shape the immune response. On the one hand they are able to initiate adaptive immune responses while on the other they are responsible for maintaining tolerance towards self antigens. Which of the two types of immune response is initiated depends largely on the signals received by the DCs at the time of antigen uptake. Vaccine strategies for cancer immunotherapy—including melanoma—are thus concentrated on the delivery—in vivo and ex vivo—of cancer antigens to this specific subset of antigen presenting cells.

In one embodiment, the present invention provides Lipovaxin for Malignant Melanoma (Lipovaxin-MM) which is a multivalent, dendritic cell (DC)—targeted liposomal vaccine/immunotherapy against malignant melanoma. In this embodiment, and as described herein, the vaccine is prepared from six components: membrane vesicles (MVs) prepared from MM200 melanoma cells, the DC-SIGN specific domain antibody (dAb) DMS5000, the chelator lipid 3(nitrilotriacetic acid)-ditetradecylamine (3NTA-DTDA), nickel sulphate ($NiSO_4$), the cytokine interferon gamma (IFN-gamma) and the lipid α-palmitoyl-β-oleoyl-phosphatidylcholine (POPC).

The membrane fraction of MM200 melanoma cells forms MVs that carry membrane-associated antigens including melanoma-associated tumour antigens. DMS-5000, a $V_H$ dAb fragment, recognises the human DC marker DC-SIGN and enables the specific delivery of the vaccine to DCs. DMS5000 is tethered, via a polyhistidine C-terminal tail, to the membrane vesicles using the chelator lipid 3NTA-DTDA and this interaction is dependent on the presence of $NiSO_4$. Insertion of 3NTA-DTDA into the membrane of the vesicles is enhanced by the inclusion of the carrier lipid POPC. The cytokine IFN-gamma provides the stimulatory signal required to arm DCs to perform their necessary effector functions.

Lipovaxin-MM is a liposomal vaccine/immunotherapy for malignant melanoma which acts by specifically targeting its antigenic cargo to the DC-SIGN receptor on the surface of human DCs in vivo. DC-SIGN is an endocytic receptor and binding of the vaccine to DC-SIGN leads to the internalisation of the vaccine-DC-SIGN complex by the DC. The vaccine also carries the cytokine IFN-gamma which stimulates DC maturation. Lipovaxin-MM has thus been designed to enable the cytokine to provide a stimulatory signal to the DCs at the same time that the DCs receive and process the antigenic material, thus providing the DCs with a better chance to initiate appropriate vaccine-specific stimulatory T cell responses. No ex vivo manipulation of patient DCs is required, which is a significant advantage over existing DC-targeted melanoma vaccines trialed to date. Co-culture of human DCs with Lipovaxin-MM in vitro leads to the internalisation of the vaccine and the up-regulation of a number of DC maturation markers including CD64, CD40, CD86, CD80 and HLA-ABC and to a lesser extent HLA-DR.

Lipovaxin-MM targets a pool of melanoma antigens, derived from the melanoma cell derived-membrane fraction, to DCs whilst at the same time delivering an appropriate stimulatory signal to ensure the optimal maturation of the targeted DCs. In the formulation described herein, Lipovaxin-MM carries general plasma-membrane markers such as Pan-cadherin, as well as melanoma-associated proteins. The presence of at least three of these proteins—gp100, tyrosinase and MART-1—has been confirmed in the vaccine. Numerous uncharacterised MM200 membrane-associated melanoma antigens are also likely to be present in the membrane vesicles that make up the vaccine, thus allowing the delivery of a complex pool of antigens to the DCs and thereby not limiting the choice of vaccine antigens to a particular melanoma differentiation or Cancer Testis (CT) antigen. Two-dimensional SDS-PAGE analysis of the membrane fraction from the MM200 melanoma cells used in Lipovaxin-MM has revealed the presence of >700 separate protein components.

DC maturation is essential to overcome T cell anergy, a phenomenon reported to be associated with tumour progression [19, 20]. To achieve this, IFN-gamma, which modulates multiple DC effector functions [21], has been included in the formulation. Since this cytokine is physically associated with the vaccine, DCs receive an appropriate stimulatory signal at the same time as the antigenic cargo reaches them.

The membrane vesicles which are integral to Lipovaxin-MM carry on their surface numerous copies of a His-tagged recombinant $V_H$ dAb (DMS5000) that was selected for its ability to specifically target the human DC surface marker DC-SIGN (DC-specific intercellular adhesion molecule 3-grabbing nonintegrin), a C-type lectin. DC-SIGN is specifically expressed by human DCs [22]. It is induced during DC differentiation, is moderately down-regulated upon the maturation of DCs [23] and is implicated in the capture and uptake of pathogens that range in size from very small pathogens such as viruses (HIV, hepatitis C virus (HCV), Ebola, dengue) to the much larger bacteria, fungi and parasites [24]. DC-SIGN is rapidly internalised upon ligand binding [25], with in vitro studies showing that antigens targeted to DC-SIGN on human DCs are rapidly endocytosed, transported to the lysosomes and presented to T cells in both an MHC Class I and Class II context [26]. The Lipovaxin-MM strategy utilises a versatile chelator lipid that allows a His-tagged molecule (such as an antibody or an antibody fragment) to associate with the surface of liposomes or membrane vesicles without the need for additional chemical modification of the engrafted molecule. In vitro, DMS5000 enables the targeted delivery of DMS5000-engrafted liposomes to human DC-SIGN expressing cells, including monocyte-derived DCs. The delivery is DMS5000-dependent and specific to human DC-SIGN. Our studies of a fluorescently tagged Lipovaxin-MM by confocal microscopy have confirmed that, in vitro, binding of the vaccine to human DCs is followed by internalisation of the vaccine. Processing of the antigens carried by Lipovaxin-MM is expected to follow. In vivo targeting of antigens to human DCs through DC-SIGN, using a grafted mouse model (mice transplanted with human immune cells), has recently been reported to elicit stimulatory immune responses and to inhibit the growth of engrafted tumours thus supporting the notion that this receptor is an effective target for the delivery of cancer antigens [27].

While a specific description of a melanoma vaccine is given herein, it will be appreciated that the composition and methods of the invention can be adapted for suitability in treatment of other tumours especially antigenic tumours including, for example, bladder, breast, lung particularly small cell lung cell carcinoma (SCLC) or non-small cell lung cell carcinoma (non-SCLC), liver, seminomas, melanoma, and/or head and neck cancers squamous cell carcinoma of the head and neck (SCCHN), colon cancer, breast cancer, glioblastoma, neuroblastoma and medullary cancer of the thyroid.

The invention is further described in the following examples, for the purposes of illustration only.

EXAMPLES

1) Physical, Chemical and Pharmaceutical Properties and Formulation

A) Drug Substance—Background

Lipovaxin-MM is prepared from 6 ingredients which make up 4 starting 'pre-formulation components'. The composition and characteristics of the Lipovaxin-MM pre-formulation components are set out in Table 1, which is shown in FIG. 13.

Membrane Vesicles

The vaccine's numerous antigens are derived from the membrane fraction of lysed MM200 melanoma cells. The MM200 cell line is a melanoma cell line that was isolated from a primary melanoma originally removed from a 43 year-old woman. HLA typing (A1,3; B7,35; DR2,4), chromosomal analysis and karyotypic analysis of the cell line have been described [28]. The MM200 cell line is reported to express the melanoma differentiation antigens tyrosinase, gp100 and MART-1, and the cancer testis antigens MAGE-A3, MAGE A-10, BAGE, GAGE and XAGE, but not MAGE-A1, CT-7, NA17-1 or NY-ESO-1[29]. Patients diagnosed with melanoma have been shown to have a high frequency of MM200-specific antibodies in their serum [30]. Unrelated clinical studies have also reported the use of this cell line for malignant melanoma vaccine studies [29, 31, 32]

This cell line has been used by others in pre-clinical studies of a vaccinia lysate MM200 melanoma vaccine and over 400 patients have received an MM200-based vaccinia lysate vaccine with no apparent adverse effect [29, 31, 32]. The MM200 cells used in Lipovaxin-MM pre-clinical studies originate from the same pool of cells used in those studies, a single ampoule (dated Jan. 28, 1994) obtained from the laboratory of Professor Peter Hersey (University of Newcastle, Oncology and Immunology Unit, Newcastle, Australia). The documentation received indicates that the 'Jan. 28, 1994' cells were harvested from a secondary culture of a 1986 primary culture and that those cells have been tested for and confirmed to be clear of contaminating adventitious agents. Adventitious agent testing has also been conducted on the cells used in the Lipovaxin-MM pre-clinical studies.

A single batch of MM200 MVs is produced from a bulk MM200 cell preparation for the production of the investigational product. MV production is based on the lysis of the MM200 cells by sonication followed by two rounds of centrifugation, low speed followed by high speed. Sonication and centrifugation for the production of the MVs is conducted in multiple 1 mL processing lots. Brief sonication assists in the formation of multilamellar vesicles that vary in size and form the antigen component of the vaccine. The vesicles carry numerous proteins including melanoma antigens.

MVs are then prepared by resuspending the membrane pellets in phosphate buffered saline (PBS). The resulting membrane fractions are subsequently pooled to generate the bulk MV material. The entire process is conducted aseptically to prevent contamination of the MV material. Terminal sterilisation is not possible. Bulk MVs are subsequently dispensed aseptically such that each vial contains sufficient material for the production of 2 mL of Lipovaxin-MM. Random aliquots are tested for the presence of adventitious agents and for their melanoma antigen profile.

3NTA-DTDA

The N-nitrilotriacetic acid (NTA)/His-tag system is widely used for the one-step isolation and purification of recombinant proteins. The tetra-dentate ligand NTA forms a hexagonal complex with divalent metal ions, such as $Ni^{2+}$, which occupy four of the six binding sites in the complex. The imidazole rings from two histidines of a string of consecutive histidine residues (also known as a His-tag) bind to the unoccupied sites of the metal ion-NTA complex. The binding is synergistic and the 2:1 (histidine:metal ion-NTA) ratio creates stable immobilisation of the His-tagged molecule.

3NTA-DTDA, as described in WO 00/64471 and WO 2005/018610, is synthesised through a six step synthesis by coupling each COOH group of the NTA head group to another NTA group. The resulting 3NTA moiety achieves a higher local density of NTA head groups that allows for a more stable anchoring of His-tagged proteins. The 3NTA head group is then linked to two 14-carbon hydrocarbon chains to produce a chelator lipid that contains a 3NTA head group covalently linked to DTDA (ditetradecylamine). Nickel ions occupy four of the six binding sites in each of the NTA groups. The two-14-carbon hydrocarbon chains form a lipid moiety that can be inserted into the lipid bilayer of liposomes [33].

POPC

POPC (α-Palmitoyl-β-Oleyol-sn-Glycero-3-Phosphocholine) is a phospholipid with 2 asymmetric hydrocarbon chains: a fully saturated 16-carbon chain and a mono-cis-unsaturated 18-carbon chain with one double bond in between the th and the 10th carbon (18:1, ). The transition temperature for POPC from gel phase to liquid crystalline phase is around −4° C. POPC, which is a normal lipid constituent of cell membranes, is widely used in the preparation of liposomes. Esperion Therapeutics, Inc (Ann Arbor, Mass.) reported a satisfactory safety profile for the repeated administration of 14-16 mg of POPC-containing liposomes every 4 days for 7 cycles (http://www.pharmaquality.com/mag/08092005/pfq_08092005_F02.html).

Synthetic liposomes consisting of a mixture of POPC with either NTA-DTDA [34-36], or 3NTA-DTDA [37, 38] are produced and fused with membrane vesicles. This effectively allows the incorporation of either of the chelator lipids into the lipid bilayer of the membrane vesicles. A His-tagged protein (such as DMS5000) is engrafted on the surface of the resulting modified membrane vesicles thus effectively coating the vesicle with a ligand which allows the vesicle to be specifically targeted to a chosen cell surface receptor. Membrane vesicles modified to contain either NTA-DTDA or 3NTA-DTDA have been used to target DCs in vivo in mouse models [37].

Nickel Sulphate

Lipovaxin-MM in its final formulation contains approximately 10 μg/mL of nickel sulphate (1:1 molar ratio of nickel sulphate to NTA-head groups), all of which is expected to be associated with the chelator lipid 3NTA-DTDA. Nickel binds NTA with high affinity ($K_d < 10^{-11}$ M). Because it is present in the same molar ratio as the NTA moiety on the head group of 3NTA-DTDA, the concentration of free nickel in Lipovaxin-MM preparations is expected to be extremely low.

Although nickel and its salts have been reported to be toxic and carcinogenic at high levels [39], the content of nickel within Lipovaxin-MM is well within acceptable levels. The general population takes in most nickel through food, with the average daily Western dietary nickel intake being 69-162 μg. Thus even the highest dose of 10 mL of Lipovaxin-MM, which contains 100 μg of nickel, represents no more than the daily dietary intake of nickel [40]. Excretion of systemically absorbed nickel is mainly through the urine; half life values are around 28 hours, and within 4 days 100% of a systemic dose of nickel is recovered in either urine or as unabsorbed nickel in stool [39]. An interesting parallel can be drawn with patients with chronic renal disease maintained on a dialysis regimen, who can absorb up to 100 μg of nickel per dialysis [41]. The investigational product, at its highest proposed dose, is expected to deliver quantities of nickel that are comparable to that type of therapy.

To prepare the liposomes, a mixture of the two lipids is prepared in PBS and supplemented with nickel and the resulting preparation is lyophilised. The liposomes are stored as a lyophilised powder which is reconstituted in water during the formulation process.

DMS5000

DMS5000 is a domain antibody (dAb) having the amino acid sequence set out in FIG. 12 (SEQ ID NO: 1; SEQ ID NO: 3) and is highly specific for the human DC cell surface receptor DC-SIGN (DC-specific intercellular adhesion molecule 3-grabbing nonintegrin). Domain antibodies are the smallest functional binding units of antibodies, and consist of the variable region of either the heavy ($V_H$) or light ($V_L$) chains of human antibodies. DMS5000 is a 14,386 kDa $V_H$ dAb, selected on the basis of its ability to facilitate binding of 3NTA-DTDA-containing liposomes to human DC-SIGN-expressing cells when engrafted onto the liposomes. The dAb sequence set out in SEQ ID NO: 1 is preceded by Ser-Thr residues which are present in the expression vector polylinker to accommodate a SalI cloning site for expression. The dAb sequence without the ST residues is set out in SEQ ID NO: 3.

DMS5000 is produced as a secreted protein using a process that involves production of the protein in E. coli followed by capture of the protein from conditioned media using Streamline Protein A.

Further contaminants are removed by anion-exchange chromatography and the remaining endotoxin is removed by passage over a Mustang E filter. Dialysis into the final formulation is followed by sterile filtration. The resulting bulk protein is finally subjected to aseptic fill and finish to produce vialed material for the clinical trial.

Figure 1:
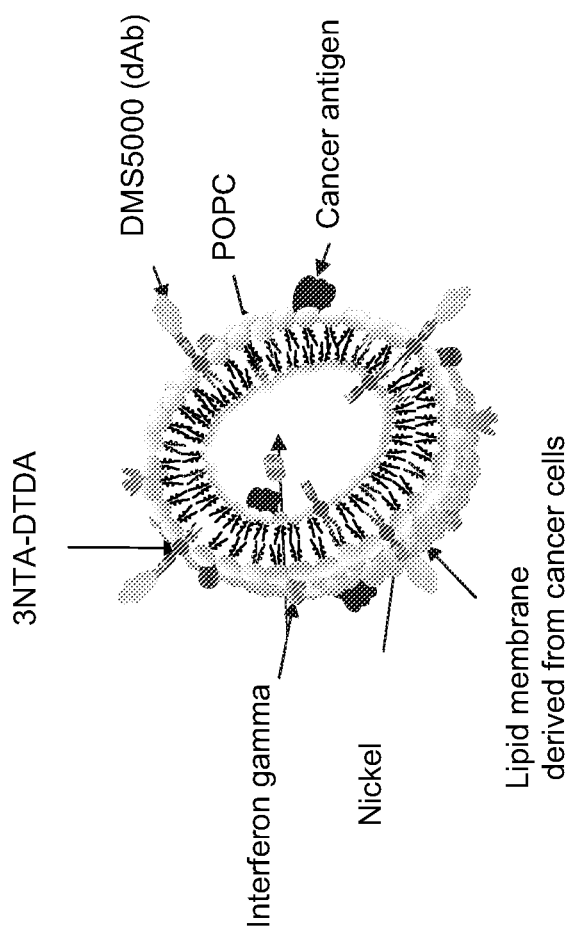
FIG. 1 Diagrammatic representation of Lipovaxin-MM showing lipids derived from the MM200 membrane fraction, POPC and various cancer antigens are visible. The dendritic cell targeting domain antibody (dAb) DMS5000 is also depicted. Interferon gamma is depicted as being mainly associated with the outer surface of the vaccine.
Figure 2:
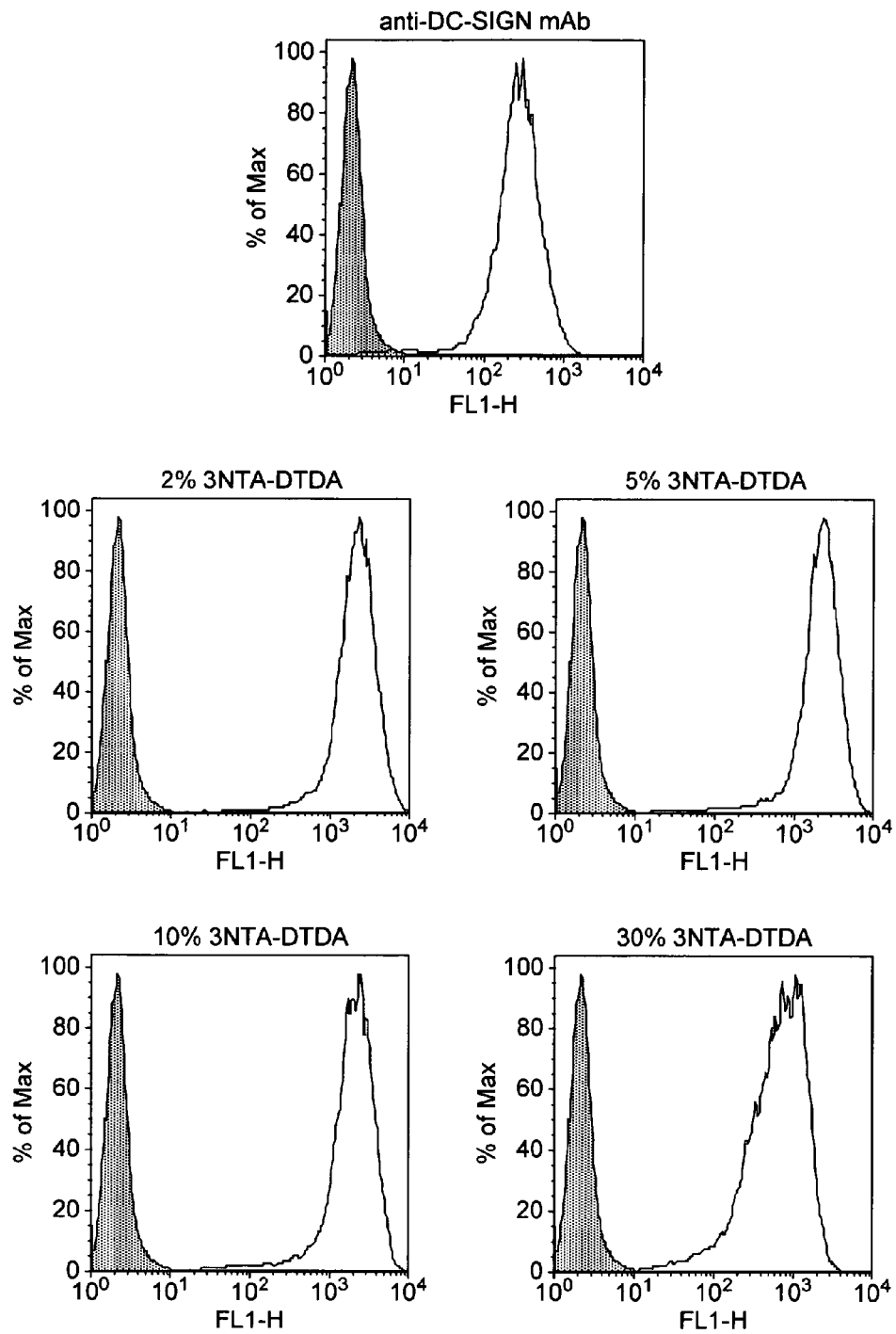
FIG. 2 Increasing the amount of 3NTA-DTDA in liposomes, and the corresponding molar ratio of dAb, does not increase the targeting effect of Lipovaxin-MM. THP-1 cells expressing human DC-SIGN were incubated with an anti-human DC-SIGN monoclonal antibody or with Lipovaxin-MM containing different amounts of 3NTA-DTDA and engrafted dAb.

A DMS5000—fluorescent liposome mixture is able to bind DC-SIGN-expressing cells—DCs or any other cell types that have been genetically modified to express exogenous human DC-SIGN (e.g. THP-1/DC-SIGN cells)—only when the chelator lipid 3NTA-DTDA is added to the liposome mixture (FIG. 2), thus confirming that association of DMS5000 with the liposomes is dependent on Ni-3NTA-DTDA.

Figure 3:
FIG. 3 Z-sections through a human monocyte-derived dendritic cell (moDC) incubated with Lipovaxin-MM. Vaccine was made from POPC, 3NTA-DTDA and MM200 membrane vesicles incorporating the BODIPY-500-510-C fluorescent dye (green) and engrafted with the dAb DMS5000. moDCs were stained with BODIPY red succinimidyl ester (red) and incubated with vaccine for 5 hours prior to microscopy. Cells were placed on coverslips immediately prior to observation under the confocal microscope. The Z-sections show both that vaccine binds to the surface of the moDC (first and fourth images) and that it is taken inside the cell (second and third images).

Confocal microscopy has enabled the visualization of the interaction between Lipovaxin-MM and DC-SIGN expressing cells—including human DCs—thus confirming not only that it binds to the target cells but also that it is internalised by the DCs. This confirms that the delivery of Lipovaxin-MM to the DC-SIGN receptor on the surface of human DCs is followed by endocytosis and internalisation of the cargo (FIG. 3).

B) Manufacturing

Each of the ingredients are manufactured in accordance with Good Laboratory Practice (GLP) and when possible the pre-formulation components are prepared in accordance with Good Manufacturing Practice (GMP), by appropriately accredited facilities The investigational product is formulated by combining the membrane vesicles with the liposomal constituent and IFN-gamma and fusing by sonication. DMS5000 is added in a final step before the investigational product is administered to the patient.

C) Properties i) Pharmacology

At the highest dose the patient receives a total of 7.449 mg POPC, 0.297 mg 3NTA-DTDA, 0.103 mg Nickel sulphate and 3.8 mg DMS5000. In these quantities they are expected to be of little pharmacological consequence.

ii) Analysis and Characterisation

Figure 4:
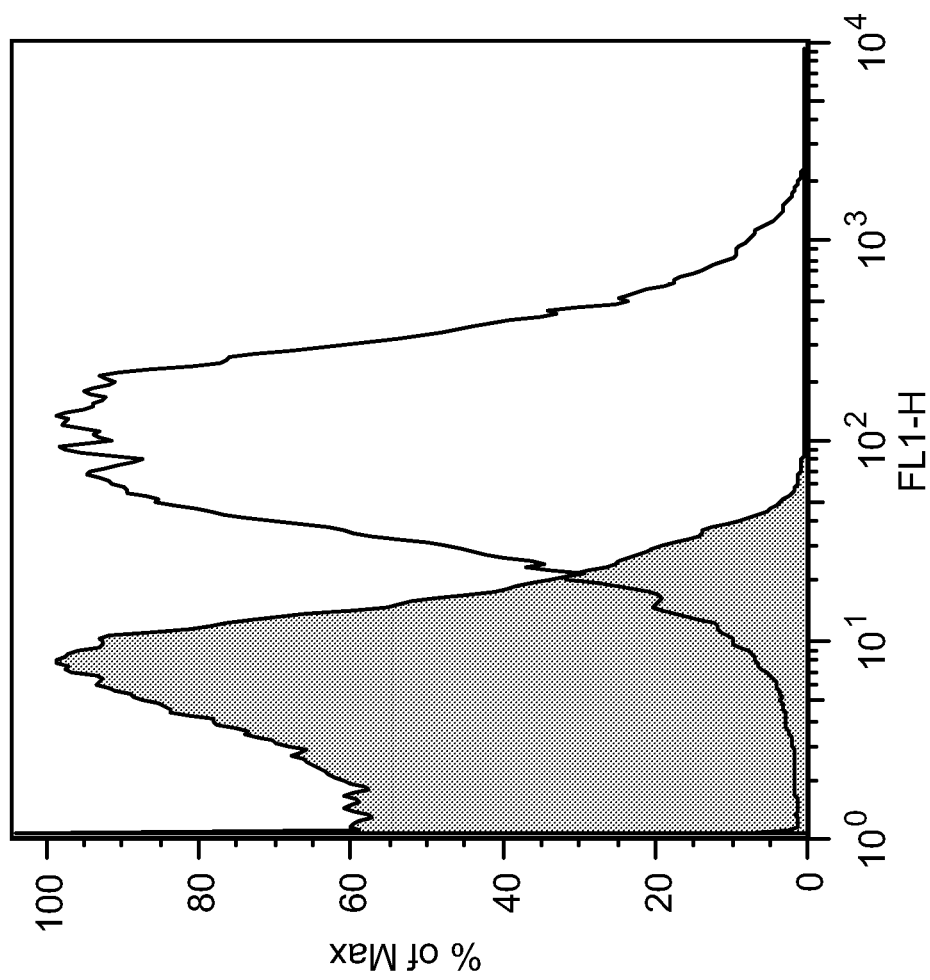
FIG. 4 Engraftment assay. Liposome/MV fusions and Lipovaxin-MM (with dAb engrafted) were incubated with Protein A-Biotin, followed by Streptavidin conjugated to the fluorochrome AlexaFluor488. Analysis by flow cytometry demonstrated that only particles which have dAb engrafted (right hand side) are able to bind the fluorochrome.

Lipovaxin-MM characterisation involves the analysis of at least four parameters, all of which are expected to directly affect the potency of the vaccine. Firstly, engraftment of DMS5000 by binding of its His-tag to Ni-3NTA-DTDA is determined (FIG. 4).

Figure 5:
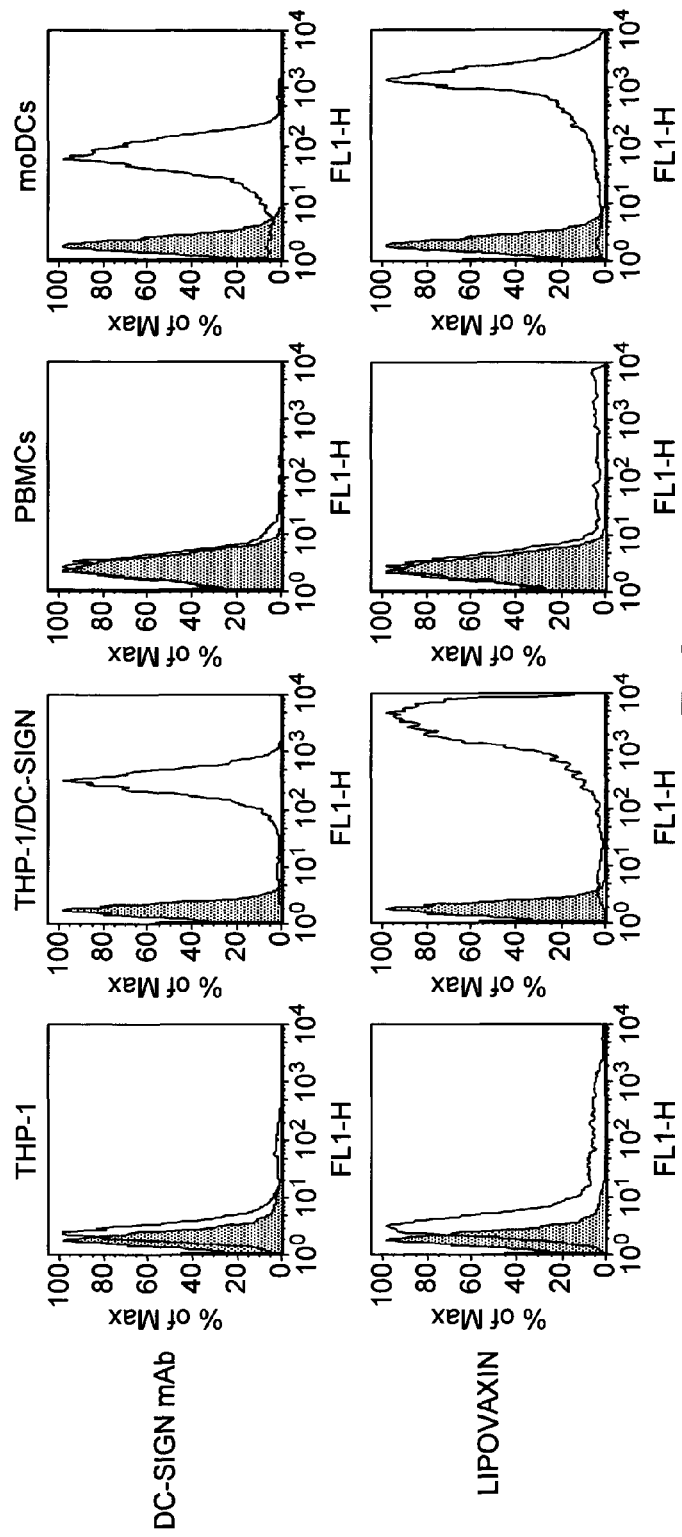
FIG. 5 Binding of fluorescinated Lipovaxin-MM to human cells and transfected cell lines. THP-1 cells, transfected THP-1 cells expressing human DC-SIGN (THP-1/DC-SIGN), human peripheral blood mononuclear cells (PBMCs), and human monocyte derived Dendritic Cells (moDCs) were assessed for DC-SIGN expression, and ability to bind fluorescinated Lipovaxin-MM. Only THP-1/DC-SIGN cells and moDCs expressed DC-SIGN, and were able to bind Lipovaxin-MM.

Secondly, the ability of the vaccine to target and bind DC-SIGN-expressing cells is confirmed in vitro (FIG. 5).

Figure 6:
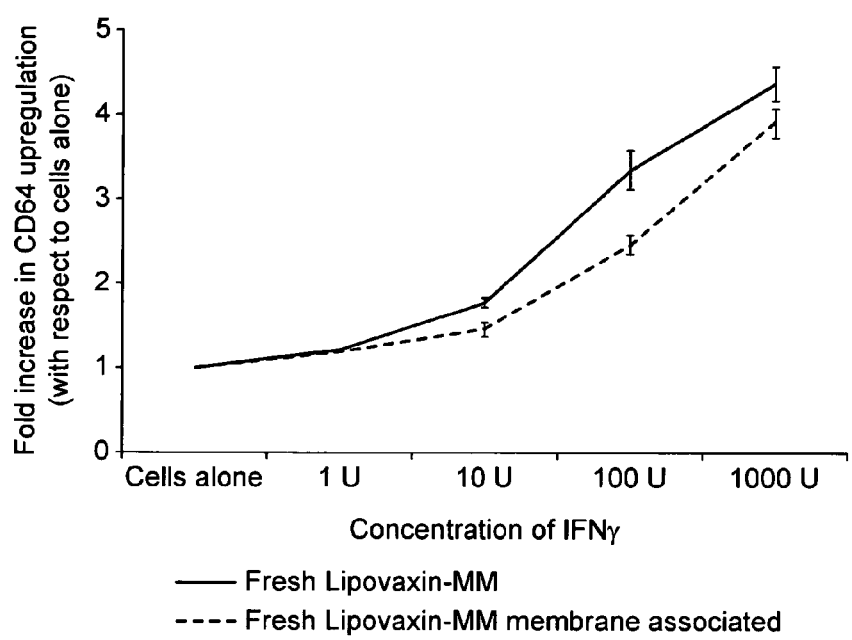
FIG. 6 Quantitation of IFN-gamma activity associated with Lipovaxin-MM. IFN-gamma activity of Lipovaxin-MM was measured based on the expression of CD64 on THP-1/DC-SIGN cells. Cells were incubated for 48 hours at 37° C. with different concentrations of either fresh Lipovaxin-MM or Lipovaxin-MM where unincorporated IFN-gamma was removed by centrifugation (Lipovaxin-MM membrane associated).

Thirdly, the vaccine preparation is analysed to confirm the physical association of the cytokine IFN-gamma with the vaccine. As Lipovaxin-MM's mode of action is highly dependent on the delivery of IFN-gamma to the target cells, association of the cytokine with the vaccine is important for its activity (FIG. 6).

Finally, the presence of melanoma-associated antigens in the vaccine preparation is confirmed by Western blot analysis (FIG. 7).

iii) Stability

The following three criteria are used to measure the stability of Lipovaxin-MM, including its stability after storage: (i) the ability of a vaccine preparation to bind human DC-SIGN-expressing cells, (ii) the proportion of IFN-gamma that remains physically associated with the vesicles and (iii) the biological activity of vaccine-bound IFN-gamma. Because Lipovaxin-MM is a liposomal vaccine, the membrane bilayers that make up the vaccine are susceptible to damage by freezing in the absence of an appropriate cryoprotectant. Storage of the investigational product is therefore only possible at temperatures at which it does not freeze. At 4° C., Lipovaxin-MM binding to DC-SIGN expressing cells remains unaltered for a period of up to 4 weeks (FIG. 8).

Total IFN-gamma activity is stable for up to 4 weeks but it appears to progressively dissociate from the vaccine with increasing storage time at 4° C. (FIG. 9).

D) Investigational Product i) Formulation

Each dose of Lipovaxin-MM is formulated by the hospital pharmacist no longer than 6 hours before it is administered to the patient. The investigational product is formulated from 4 pre-mix components: MM200 membrane vesicles, lyophilised POPC/Ni-3NTA-DTDA liposomes, IFN-gamma and DMS5000. For the 0.1 mL and 1 mL doses, 2 mL of investigational product are prepared; for the 10 mL dose 6×2 mL of investigational product are prepared and pooled before being administered to the patient.

DMS5000 having the sequence set out in SEQ ID NO: 1 is produced as a secreted protein in *E. coli* BL21(DE3) containing the vector pET30-GAS-DMS5000. pET30-GAS-DM5000 is a derivative of pET30 (Invitrogen) which incorporates the universal GAS leader signal peptide (described, for example in WO 2005/093074) at the N-terminal end of DM5000. The protein is purified from the culture supernatant of the fermentation batch by a series of chromatography steps including Streamline PrA (to capture correctly folded dAb molecules), SP Sepharose (cation exchange purification) and Mustang E (to remove endotoxin contaminants). Purity was shown to be >95% by Isoelectric Focusing, >95% by Size Exclusion Chromatography and >80% by Reverse Phase-High Pressure Liquid Chromatography. Endotoxin levels were <50 EU/ml. The resulting protein is formulated in PBS (1 mg/ml) for use in the production of Lipovaxin-MM.

Aseptic fill and finish of the bulk material is conducted in an appropriate facility to produce 1 mL lots in glass vials.

13 g of 3NTA-DTDA is produced in accordance with the published synthesis protocol (45) and shown to be of >89% purity.

GMP grade POPC was purchased from Avanti Polar Lipids (catalog number 770557, Lot# GN160181PC-23).

Puratronic® grade $NiSO_4$ (99.9985%) has been purchased from Alfa Aesar, Johnson Matthey GmbH & Co. KG (Zeppelinstrasse 7—D-76185 Karlsruhe, Germany); stock number 10820 batch number 22818; CAS# 15244-37-8. The material was filter sterilised and dispensed by aseptic fill and finish at 0.6 mg/L in sterile water at 2 mL per vial (1.2 mg $NiSO_4$sulphate per vial) by the Canberra-based company RadPharm Scientific.

Lyophilised liposomes are prepared as follows: 3NTA-DTDA is formulated in PBS and POPC in ethanol. Each solution is filter sterilized and then mixed. Sterile $NiSO_4$ is added to the mixture which is aseptically dispensed into individual vials once mixing is complete in quantities sufficient to produce 2 mL of investigational product. The material is finally freeze-dried and tested for sterility, purity and activity. Stability of the stored material is tested at regular intervals until the last patient has completed his/her vaccination schedule.

Bulk antigen is prepared as follows: Production entails the propagation of the MM200 cells in serum-free AIM-V media (catalog number 0870112DK), the harvesting of those cells in PBS and finally the production of membrane vesicles also in PBS. Prior to vesicle production, harvested cells are tested for adventitious agents and purity.

Random aliquots of the membrane vesicle preparations are also tested for adventitious agents and melanoma antigen presence.

ii) Final Dosage Form and Presentation

The investigational product is formulated in PBS. When 10 mL of investigational product is administered, 6 (six) batches of Lipovaxin-MM are prepared and the batches combined in a single vial following formulation, before the investigational product is administered to the patient. Formulation and batch-pooling is carried out in a Class II laminar Flow cabinet using aseptic technique by the hospital pharmacist.

The investigational product is cloudy in appearance and has a tendency to settle when left undisturbed (the granular appearance of the investigational product correlates with the successful engraftment of DMS5000 on the surface of the vesicles).

iii) Storage and Handling

Lipovaxin-MM pre-formulation components should be stored at –20° C., with the exception of IFN-gamma (Imukin, Boehringer Ingelheim, Germany) which should be stored at 4° C. as recommended by the manufacturer. Once formulated at the hospital pharmacy, the investigational product is stored at 4° C. for no longer than 6 hours.

The investigational product must be mixed by repeated inversion of the vial but must not be vortexed prior to its administration to the subjects.

iv) Administration

The composition is administered by direct slow intravenous administration.

2) In Vitro Studies: Lipovaxin-MM Effect on DC Markers

Monocyte-derived dendritic cells generated in vitro can be used to test the specific effect of Lipovaxin-MM on DC maturation. To achieve this monocyte progenitor cells are prepared from peripheral blood mononuclear cells that are cultured in vitro in the presence of a mixture of IL-4 and GM-CSF for 5-6 days, at the end of which period those cells express the marker DC-SIGN. When Lipovaxin-MM is co-cultured with human monocyte-derived DCs in vitro, a number of DC maturation markers including CD64, CD40, CD86, CD80 and HLA-ABC and to a lesser extent HLA-DR are upregulated and the cytokine IL-12 is detected in the conditioned media. Upregulation of the markers occurs only when the vaccine carries IFN-gamma, confirming that in vitro the delivery of the antigen alone can stimulate adequate maturation and is highest when specifically delivered to DCs via DC-SIGN targeting.

Evidence from non-clinical studies suggests that in vitro Lipovaxin-MM is able to target specifically the human DC marker DC-SIGN for the delivery of its antigenic cargo to DCs, most likely via the endocytic pathway triggered by this receptor. Targeting of Lipovaxin-MM to DC-SIGN is also accompanied by a specific increase in DC maturation cell surface markers, as well as in the production of IL-12, a cytokine important in the differentiation of naive T cells into Th1 cells.

3) Non-Clinical Studies

In vivo, studies have been limited to those animal species that are known to express DC-SIGN homologues with patterns consistent with those seen in humans. Two species have been used, the common marmoset and the macaque, but only the macaque was eventually found to be relevant for immunogenicity studies. In macaques, Lipovaxin-MM was shown to induce cell-mediated and humoral immune responses at the two doses tested, despite the fact that in vitro its ability to bind/target macaque DC-SIGN was shown to be significantly lower than its ability to bind/target human DC-SIGN. Even at the highest dose no significant adverse effects were seen with the exception of one transient increase in AST levels and one transient increase in ALT levels seen only seven days after the second dose in two different animals. Cholesterol, triglyceride and LDL levels were consistently lower at the end of the study in all four animals compared with pre-vaccination levels whilst HDL levels were consistently higher after the four vaccination series in all four animals.

i) Proof of Concept Studies in a Mouse Model

SUMMARY: A proof of concept study for the Lipovaxin platform was conducted in mice. Because DC-SIGN is not expressed by mouse dendritic cells, this study investigated the targeting of a vaccine to the DEC-205 receptor, a C-type lectin expressed by mouse DCs. The study showed that a crude preparation of membrane vesicles from the highly metastatic murine melanoma (B16-OVA)can be targeted to DCs in vivo to elicit functional effects. When used in syngeneic mice, the B16-OVA vaccine stimulated strong CTL responses in splenic T cells and induced marked protection against tumour growth. Protection was dependent on the simultaneous delivery of both antigen and DC maturation signal. Administration of the B16-OVA-DC targeted vaccine to mice challenged with B16-OVA cells induced a dramatic immunotherapeutic effect and prolonged disease-free survival.

IN DETAIL: An animal study was conducted to test the Lipovaxin platform technology in the murine B16-OVA melanoma cancer model [37]. The formulation of the vaccine used in this study differs from Lipovaxin-MM and is specific for this animal model. The murine B16-OVA melanoma cancer model is a highly metastatic tumour which when inoculated intravenously into mice causes cancer and death in the animals through its ability to metastasize, initially to the lungs, and subsequently to other organs. The Lipovaxin platform was used to construct a vaccine prepared either from cultured B16-OVA cells or in the form of liposomes modified to incorporate the OVA or SIINFEKL peptide. In all cases targeting to DCs was ensured using ScFv specific for the marker DEC-205 and the immunomodulatory cytokine interferon gamma was included as the 'danger signal'. Groups of six C57B1/6 mice were inoculated with $1.5 \times 10^5$ B16-OVA melanoma cells, and then either PBS or a vaccine (comprising $2 \times 10^5$ cell equivalents of ScFv-engrafted B16-OVA-derived MV) was administered intravenously to the mice at days 3, 6 and after tumour inoculation. Control animals developed a massive tumour load with an average of 250±37 tumor foci in the lungs by day 16 (animals were euthanised at day 22). In sharp contrast, vaccinated mice did not show any signs of tumor development up to 8 months after tumor challenge. The modified MVs also induced protective immunity against tumours in this system. Mice immunised with the vaccine (comprising $2 \times 10^5$ cell equivalents of ScFv-engrafted B16-OVA-derived MV) were examined for their ability to resist an i.v. challenge with B16-OVA cells. When lung metastases were quantified 16 days after tumour challenge, vaccinated mice showed a much lower number of metastases compared to control mice but only when a "danger signal" IFN-gamma or LPS was incorporated into the vaccine. The study successfully demonstrated that splenocytes isolated from mice vaccinated with the modified MVs showed maximum CTL activity when the MVs were targeted to DC (either via DEC205 or CD11c) and included a relevant danger signal (IFN-gamma or LPS). The study thus confirms that the vaccine produced using the Lipovaxin technology is effective at inhibiting B16-OVA tumour growth and metastasis in this animal model and that this approach can greatly simplify current strategies used for DC-based cancer vaccine production and immunotherapy in humans.

ii) Lipovaxin-MM Marmoset Study

SUMMARY: An initial study of Lipovaxin-MM was conducted in the common marmoset (*Callithrix jacchus*), the smallest non-human primate used in biomedical research. In the marmoset, DC-SIGN expression is detected in the spleen and lymph node by immunohistochemistry (using an anti-human DC-SIGN mAb). When the marmoset study was initiated, a certain degree of cross-reactivity between DMS5000 and marmoset DC-SIGN was expected but could not be confirmed. Animals received 5 doses of 0.06 mL of vaccine at weekly intervals (a dose that is equivalent to a human dose of 10 mL scaled based on weight in the marmoset). The treatment was well tolerated but no significant evidence of immunogenicity was observed. The 'danger signal', (human) IFN-gamma, included in the formulation was subsequently found to have reduced biological activity in vitro when used to stimulate marmoset peripheral blood monocytes. This was identified as a possible cause for the apparent lack of immunogenicity of Lipovaxin-MM in these animals. Since completion of that study, the cloning of marmoset DC-SIGN gene has facilitated more extensive binding studies using cells that have been modified to express marmoset DC-SIGN. Those studies now indicate that binding of Lipovaxin-MM to marmoset DC-SIGN is minimal, at least in vitro. The apparent reduced affinity of Lipovaxin-MM for marmoset DC-SIGN in combination with the reduced activity of IFN-gamma in those animals would have significantly impaired the ability of Lipovaxin-MM to induce a detectable immune response in those animals.

IN DETAIL: The common marmoset (*Callithrix jacchus*) is the smallest non-human primate used in biomedical research. In the marmoset, DC-SIGN expression is detected in the spleen and lymph node by immunohistochemistry (using an anti-human DC-SIGN mAb). When the marmoset study was initiated, a certain degree of cross-reactivity between DMS5000 and marmoset DC-SIGN was expected. Two groups of animals (3 animals in each group) received 5 doses of 0.06 mL of vaccine at weekly intervals. The two groups differed in the dAb used to engraft on the surface of the vaccine—one group received vaccine engrafted with DMS5000 and the second was engrafted with a 'dummy dAb' (a dAb with no specific target). There were no serious adverse effects associated with the repeated administration of either of the two vaccines at a dose equivalent to a human dose of 10 mL (scaled based on weight in the marmoset). Animal weights were relatively stable. No significant changes in hematological parameters were observed. Leukocyte subset analysis identified an increase in circulating myeloid DCs in all six animals. Animals that had received the targeted vaccine showed a decrease in circulating plasmacytoid DCs. A rash was reported after dose 1 that was most pronounced on the abdomen of animals that had received the non-targeted Lipovaxin-MM. The rash recurred in animals of the non-targeted vaccine group after dose 5 only. None of the animals appeared to be in any discomfort. No significant evidence of immunogenicity was observed. The 'danger signal', (human) IFN-gamma, included in the formulation was subsequently found to have reduced biological activity in vitro when used to stimulate marmoset peripheral blood monocytes. This was identified as a possible cause for the apparent lack of immunogenicity. Since completion of that study, the cloning of marmoset DC-SIGN gene has facilitated more extensive binding studies using cells that have been modified to express marmoset DC-SIGN. These studies now indicate that binding of Lipovaxin-MM to marmoset DC-SIGN is minimal, at least in vitro.

iii) Lipovaxin-MM Immunogenicity in Pigtailed Macaques

SUMMARY: A final test of Lipovaxin-MM was conducted in the non-human primate *Macaca nemestrina* (pigtailed macaque). This animal species was selected because the macaque DC-SIGN receptor is highly conserved at the amino acid level compared to its human counterpart and performs an analogous function as an endocytic receptor. The tissue distribution of DC-SIGN-expressing cells in the macaque also generally corresponds with that seen in human tissues with only some minor differences. Two groups of animals were tested in the study that differed in the doses of the vaccine administered to the animals. Four animals were administered three 0.6 mL doses of Lipovaxin-MM (which is equivalent to a human dose of 10 mL scaled down based on body weight) and four animals were administered 5 mL doses of Lipovaxin-MM (50% of the highest proposed human dose, not adjusted for animal weight) at 4 week intervals. The vaccine was administered intravenously under sedation into the saphenous vein. Although in vitro binding studies of Lipovaxin-MM to macaque DC-SIGN had established that the dAb binds with much lower affinity to the macaque DC-SIGN receptor than it does to its human counterpart, the study confirmed that the vaccine was able to induce detectable levels of vaccine-specific antibodies that were most evident in animals of the higher dose group and a cell-mediated response (detected based on the production of cytokines by PBMCs collected after vaccination) that was most evident in animals of the lower group.

IN DETAIL: A study of Lipovaxin-MM was conducted in the pigtailed macaque (*Macaca nemestrina*). Human IFN-gamma was confirmed to be biologically active through in vitro stimulation assays of pigtailed macaque peripheral blood mononuclear cells (PBMCs). There were therefore no doubts about the biological activity of the vaccine's danger signal. Macaque DC-SIGN amino acid sequences are readily accessible and known to be ~93% identical to the amino acid sequence of human DC-SIGN in the lectin binding region— the same region that was used to generate DMS5000. Because many of the monoclonal antibodies raised against human DC-SIGN are known to cross-react with macaque DC-SIGN [42, 43], a certain degree of cross-reactivity of DMS5000 to macaque DC-SIGN had been anticipated. In vitro studies of Lipovaxin-MM using both monocyte-derived macaque DCs and THP-1 cells that had been modified to express exogenous macaque DC-SIGN identified however that DMS5000 had a lower affinity for pigtailed macaque DC-SIGN than human DC-SIGN. The study of Lipovaxin-MM in 8 pigtailed macaques was designed to provide safety and immunogenicity information to support an application for a first-in-human Phase I clinical trial. Given that Lipovaxin-MM was shown to target macaque DC-SIGN with lower affinity than human DC-SIGN, it was understood that the study might underestimate the potential immunogenicity of the vaccine in this animal model. Two doses (0.6 mL and 5 mL) were tested in the study. The lower dose is equivalent to a human dose of 10 mL scaled down based on an average human weight of 70 kg and animal weight of 4 kg. The higher dose is equivalent to 50% of the absolute volume of the highest proposed human dose which was also the maximum volume that could be administered to the animal under the guidelines of the animal facility. This is equivalent to approximately 8 times the highest human dose if it were scaled based on macaque body weight. The macaques were divided into two groups of four animals. The first group received 3 doses of 0.6 mL Lipovaxin-MM at 4 week intervals and the second group received 3 doses of 5 mL Lipovaxin-MM. Animals in the second group also received an additional dose of Lipovaxin-MM 7 days after dose 3 as recommended by WHO guidelines. All four animals were sacrificed 7 days after this fourth dose as part of a safety study. Both doses of Lipovaxin-MM resulted in the production of the cytokines IFN-gamma, TNF-alpha and IL-6 by PBMCs as early as 7 days after the first dose (FIG. 9), but Lipovaxin-MM-specific antibodies were detected only in animals receiving the higher dose of Lipovaxin-MM. This indicates that in the macaques the type of immune response induced by Lipovaxin-MM was affected by the dose of vaccine administered and that the lower dose of vaccine appeared to be effective at stimulating cell-mediated immune responses (which are critical to an anti-tumour response) while the higher dose was able to induce humoral immunity. Thus, despite the lower affinity of DMS5000 for macaque DC-SIGN, Lipovaxin-MM was able to stimulate a detectable vaccine-specific immune response in vaccinated animals.

a) Summary

In the pigtailed macaque study outlined above, four animals were administered 4 doses of 5 mL of Lipovaxin-MM (50% of the actual highest proposed human dose). The vaccine was well tolerated and safe when administered at that dose. The only abnormal readouts were observed at day 35 when an increase in aminotransferase levels was observed in two animals (two different enzymes in the two different animals). The increase was transient as it was not observed after dose 3 or 4 for those two animals, or any other animals in the study. At necropsy, multifocal follicular hyperplasia was observed in the spleen and lymph nodes. This observation suggests that Lipovaxin-MM has been processed by DCs. Hyperplasia of lymphoid tissue was also identified in the lungs, intestine and liver for all animals. Expression of DC-SIGN has been reported for DCs in all three organs in both humans and macaques. Thus, despite the lower affinity of DMS-5000 for macaque DC-SIGN, the vaccine successfully induced a reaction in those immune organs that have been reported to express DC-SIGN. The visibly increased reactivity of the lymphoid organs indicates an active immune response.

b) Haematology

At each blood draw, a routine haematology test panel was conducted which included white cell counts, red cell counts and platelet counts. Hemoglobin, hematocrit, MCV and MCHC levels were also assessed. Test results were compared to published 'normal' values for macaques.

Total white cell counts varied for each individual at the various time points but did not show a consistent trend. Total red blood cell counts remained relatively unchanged over the period of the study. All values appeared to be within the 'normal' range. It was noted that with the exception of one animal, the percentage of lymphocytes in peripheral blood at the end of the study was generally higher than at the beginning of the study. Conversely, neutrophil percentages were generally lower at the end of the study compared with initial values.

c) Blood Biochemistry

Animal liver function was monitored following administration of Lipovaxin-MM based on blood aminotransferase levels for aspartate aminotransferase (AST or SGOT) and alanine aminotransferase (ALT or SGPT). The levels of both enzymes varied significantly between each of the animals at the various time points but were generally within published 'normal' levels with the exception of two readings at day 35 of the study. At day 35 a high AST level was observed in one animal and a high ALT level was identified in a second. Both values were elevated beyond normal values at day 35 of the study but not at day 42 or at any subsequent time point; these are listed in Table 2.

TABLE 2

Macaque liver AST and ALT levels throughout the toxicology study.

| | Animal # 2.5407 | | Animal # 2.536 | | Animal # 8874 | | Animal # 6105 | |
|---|---|---|---|---|---|---|---|---|
| | AST | ALT | AST | ALT | AST | ALT | AST | ALT |
| Day 0 | 64 | 45 | 85 | 52 | 40 | 27 | 23 | 37 |
| Day 7 | 66 | 44 | 65 | 46 | 29 | 26 | 21 | 33 |
| Day 35 | 82 | <u>150</u> | 51 | 38 | <u>166</u> | 55 | 30 | 29 |
| Day 42 | 65 | 61 | 50 | 32 | 24 | 44 | 16 | 61 |
| Day 63 | 72 | 67 | 39 | 33 | 24 | 29 | 20 | 32 |
| Day 70 | 59 | 60 | 59 | 45 | 34 | 26 | 22 | 24 |

The two abnormal readings observed at day 35 of the study are underlined.
AST = aspartate aminotransferase,
ALT = alanine aminotransferase, enzyme activity measured in units per litre.

d) Necropsy

Histopathology examination revealed multifocal follicular hyperplasia of all lymphoid tissue, which is consistent with a cellular immune response. Multifocal follicular hyperplasia was observed in the spleen, lung and intestines of all animals (Table 3).

Liver samples from two out of the four animals showed evidence of mild multifocal perivascular mononuclear cell infiltration. The same two animals had returned high AST and ALT results on day 35 of the study.

TABLE 3

Summary of histopathology examination conducted as part of the toxicology study.

| | B1 (2.5407) Observations | B2 (2.5360) Observations | B3 (8874) Observations | B4 (6105) Observations |
|---|---|---|---|---|
| Cerebrum | NSL | NSL | NSL | NSL |
| Cerebellum | NSL | NSL | NSL | NSL |
| Liver | mild multifocal perivascular mononuclear cell infiltration | NSL | mild multifocal perivascular mononuclear cell infiltration | mild hydropic degeneration |
| Spleen | multifocal follicular hyperplasia (white pulp) | multifocal follicular hyperplasia (white pulp) | multifocal follicular hyperplasia (white pulp) | multifocal follicular hyperplasia (white pulp) |
| Lungs | mild multifocal lymphoid tissue hyperplasia | mild multifocal lymphoid tissue hyperplasia | mild multifocal lymphoid tissue hyperplasia | vascular congestion, mild multifocal lymphoid tissue hyperplasia |
| Kidney | NSL | NSL | NSL | NSL |
| Heart | NSL | NSL | NSL | NSL |
| Pancreas | NSL | NSL | NSL | NSL |
| Testis | NSL | — | NSL | — |
| Ovary | — | NSL | — | NSL |
| Uterus | — | NSL | — | NSL |
| Lymph node | multifocal follicular hyperplasia | multifocal follicular hyperplasia | multifocal follicular hyperplasia | multifocal follicular hyperplasia |
| Trachea | NSL | hyaline cartilage mineralization | NSL | NSL |
| Muscle | NSL | NSL | NSL | NSL |
| Adrenal | NSL | NSL | NSL | NSL |
| Urinary Bladder | NSL | NSL | NSL | NSL |
| Stomach | NSL | NSL | NSL | NSL |
| Intestine | mild multifocal lymphoid tissue hyperplasia | mild multifocal lymphoid tissue hyperplasia | mild multifocal lymphoid tissue hyperplasia | mild multifocal lymphoid tissue hyperplasia |
| Skin and vein biopsy of low extremity: | | | | |
| Right | NSL | NSL | NSL | NSL |
| Left | NSL | NSL | NSL | NSL |

NSL: No Specific Lesion e) Toxicology

This study was conducted as an extension to the efficacy study of Lipovaxin-MM described above. The four animals that had received the highest dose (5 mL) received a fourth dose after which the animals were sacrificed for necropsy. Animals were monitored closely following administration of the vaccine, and blood haematology and biochemical analysis was conducted before and after each vaccination. The vaccine was well tolerated when administered at the 5 mL dose. The only significant adverse effect that could be related to the vaccine was an increase in aminotransferase levels observed one week after dose 2, in two different animals (one animal had a 3.4-fold increase in alanine aminotransferase (ALT) compared to readings obtained before administration of the second dose, while the second animal had a 5.7-fold increase in aspartate aminotransferase (AST)). The increase was transient and it is possible that it was artefactual. It was not observed in a further test conducted 7 days after the abnormal reading, nor was it observed anytime after dose 3 or 4 for those two animals, or any other animals in the study. During the study, cholesterol, triglyceride and LDL levels were found to be consistently lower at the end of the study in all four animals when compared to the levels seen before the vaccination regime started, whilst HDL levels were consistently higher after the four vaccination series in all four animals. The significance of this observation is unclear. Haematology and other blood biochemistry parameters did not show any particular trends.

At necropsy, multifocal follicular hyperplasia was observed in the spleen and lymph nodes; both organs are rich in DC-SIGN-expressing cells in both humans and macaques. The high level of activity seen in these organs of the immune system suggests that Lipovaxin-MM was successfully processed by cells of the immune system and that an active immune response was generated. Hyperplasia of lymphoid tissue was also identified in the lungs, intestine and liver for all animals. Expression of DC-SIGN has also been reported for DCs in all three organs in both humans and macaques.

This finding reflects that, despite the lower affinity of DMS-5000 for macaque DC-SIGN, the vaccine appears to have successfully stimulated an immune response in those organs that have high levels of DC-SIGN-expressing DCs, as identified by the visibly increased reactivity of all lymphoid organs.

4) Dose Justification

Because Lipovaxin-MM is a cell-derived vaccine/immunotherapy, Lipovaxin-MM doses can be described based on the number of cells that are used to derive the 'antigenic' fraction of the final product. In our studies, 1 mL of Lipovaxin-MM is prepared using membrane fraction material derived from $10^7$ MM200 melanoma cells, that is combined with POPC (0.98 mmol), 3NTA-DTDA (0.02 mmol), $NiSO_4$ (0.06 mmol) and DMS5000 (0.026 mmol), with DMS5000 being added at an ~1.3-fold excess to 3NTA-DTDA to ensure that all 3NTA-head groups are occupied.

A pre-clinical study of a related DEC-205-targeted 3NTA-DTDA based vaccine (DEC-205 is another DC expressed C-type lectin) in mice [37] used a vaccine prepared from $2 \times 10^5$ cells per dose. A minimum effective dose had not been sought for this DC-targeted vaccine in the mouse model. If this antigenic dose were to be escalated, based on weight, a clinical dose would require the use of antigenic material derived from $5.6 \times 10^8$ cells. This first-in-man study investigates three doses of Lipovaxin-MM through an adaptive design dose escalating study. The starting dose to be used in the study is guided by the macaque toxicity study. If scaled based on average human weight of 70 Kg and average macaque weight of 4 Kg, 1 mL of Lipovaxin-MM in humans equates with 0.06 mL in macaques. The starting dose of 0.1 is therefore ⅙th of the absolute lowest dose volume given to the macaques or if adjusted based on weight it would be equivalent to 0.006 mL being given to macaque, this is well below the lowest dose administered to those animals. The highest planned dose of 10 mL is 2× the highest absolute volume given to macaques. It is noted that the macaques had transient transaminase elevation with histopathological changes of monocyte infiltration into the liver at dose of 5 mL which equates to 87.5 mL dose in humans (if adjusted based in average human weight of 70 Kg and average macaque weight of 4 Kg). A 10 fold escalation is planned between cohorts, and this is consistent with dose escalation in vaccine studies. However, if the immunogenicity and/or safety signals (e.g. robust immune response with transient grade 2 elevation of transaminase) suggest a concern with 10 fold escalation an intermediate dose is chosen.

In comparison, unrelated Phase II studies have been conducted that used an MM200-based melanoma vaccine that was formulated from vaccinia virus-infected MM200 cell lysates prepared from $5 \times 10^6$ MM200 cells, and that dose was shown to be immunogenic [31, 32]. Thus for this study, 3 doses of vaccine have been chosen that cover $1 \times 10^6$ cell equivalents to $1 \times 10^7$ cell equivalents and $1 \times 10^8$ cell equivalents, respectively.

While this invention has been particularly shown and described with references to embodiments thereof, it will be understood by those skilled in the art that various changes in form and details may be made therein without departing from the scope of the invention encompassed by the appended claims.

References

1. American Cancer Society. 2008 [cited Sep. 9, 2008]; Available from: http://www.cancer.org/docroot/CRI/content/CRI_2_4_1X_What_are_the_key_statistics_for_melanoma 50.asp?sitearea=
2. (AACR), A.I.o.H.a.W.A.a.A.A.o.c.r., *Cancer in Australia* 2001, in *Cancer Series*. 2004, AIHW: Canberra.
3. Cummins, D. L., et al., *Cutaneous malignant melanoma*. Mayo Clin Proc, 2006. 81(4): p. 500-7.
4. Chang, A. E., L. H. Karnell, and H. R. Menck, *The National Cancer Data Base report on cutaneous and noncutaneous melanoma: a summary of* 84,836 *cases from the past decade. The American College of Surgeons Commission on Cancer and the American Cancer Society*. Cancer, 1998. 83(8): p. 1664-78.
5. American Cancer Society. 2008 Jun. 5, 2008 [cited Sep. 6, 2008]; Available from: http://www.cancer.org/docroot/CRI/content/CRI_2_4_3X_How_is_melanoma_staged 50.asp?sitearea=.
6. Balch, C. M., et al., *New TNM melanoma staging system: linking biology and natural history to clinical outcomes*. Semin Surg Oncol, 2003. 21(1): p. 43-52.
7. Atallah, E. and L. Flaherty, *Treatment of metastatic malignant melanoma*. Curr Treat Options Oncol, 2005. 6(3): p. 185-93.
8. Ang, K. K., et al., *Postoperative radiotherapy for cutaneous melanoma of the head and neck region*. Int J Radiat Oncol Biol Phys, 1994. 30(4): p. 795-8.
9. Lens, M. B. and T. G. Eisen, *Systemic chemotherapy in the treatment of malignant melanoma*. Expert Opin Pharmacother, 2003. 4(12): p. 2205-11.
10. Spiro, T., L. Liu, and S. Gerson, *New cytotoxic agents for the treatment of metastatic malignant melanoma: temozolomide and related alkylating agents in combination with guanine analogues to abrogate drug resistance*. Forum (Genova), 2000. 10(3): p. 274-85.
11. Strannegard, O., F. B. Thoren, and E. Lundgren, [*Interferon-alpha can improve the prognosis in high-risk melanoma. Combination of surgery, cytostatics and natural IFN-alpha doubled the survival rate*]. Lakartidningen, 2008. 105(6): p. 358-61.
12. Hauschild, A., et al., *Practical guidelines for the management of interferon-alpha-2b side effects in patients receiving adjuvant treatment for melanoma: expert opinion*. Cancer, 2008. 112(5): p. 982-94.
13. Rosenberg, S. A., et al., *Treatment of 283 consecutive patients with metastatic melanoma or renal cell cancer using high-dose bolus interleukin 2*. JAMA, 1994. 271(12): p. 907-13.
14. Smith, F. O., et al., *Treatment of metastatic melanoma using interleukin-2 alone or in conjunction with vaccines*. Clin Cancer Res, 2008. 14(17): p. 5610-8.
15. van Houdt, I. S., et al., *Favorable outcome in clinically stage II melanoma patients is associated with the presence of activated tumor infiltrating T-lymphocytes and preserved MHC class I antigen expression*. Int J Cancer, 2008. 123(3): p. 609-15.
16. Danson, S. and P. Lorigan, *Melanoma vaccines—they should work*. Ann Oncol, 2006. 17(4): p. 539-41.
17. Steinman, R. M. and I. Mellman, *Immunotherapy: bewitched, bothered, and bewildered no more*. Science, 2004. 305(5681): p. 197-200.
18. Wang, T., et al., *Regulation of the innate and adaptive immune responses by Stat-3 signaling in tumor cells*. Nat Med, 2004. 10(1): p. 48-54.
19. Seliger, B., *Strategies of tumor immune evasion*. BioDrugs, 2005. 19(6): p. 347-54.
20. Pinzon-Charry, A., T. Maxwell, and J. A. Lopez, *Dendritic cell dysfunction in cancer: a mechanism for immunosuppression*. Immunol Cell Biol, 2005. 83(5): p. 451-61.

21. Frasca, L., et al., *IFN-{gamma} Arms Human Dendritic Cells to Perform Multiple Effector Functions*. J Immunol, 2008. 180(3): p. 1471-1481.
22. Geijtenbeek, T. B., et al., *Identification of DC-SIGN, a novel dendritic cell-specific ICAM-3 receptor that supports primary immune responses*. Cell, 2000. 100(5): p. 575-85.
23. Engering, A., et al., *The Dendritic Cell-Specific Adhesion Receptor DC-SIGN Internalizes Antigen for Presentation to T Cells*. J Immunol, 2002. 168(5): p. 2118-2126.
24. Geijtenbeek, T. B. H., et al., *Self- and Nonself-Recognition by C-Type Lectins on Dendritic Cells*. Annual Review of Immunology, 2004. 22(1): p. 33-54.
25. Engering, A., et al., *The dendritic cell-specific adhesion receptor DC-SIGN internalizes antigen for presentation to T cells*. J Immunol, 2002. 168(5): p. 2118-26.
26. Tacken, P. J., et al., *Effective induction of naive and recall T-cell responses by targeting antigen to human dendritic cells via a humanized anti-DC-SIGN antibody*. Blood, 2005. 106(4): p. 1278-1285.
27. Kretz-Rommel, A., et al., *In vivo targeting of antigens to human dendritic cells through DC-SIGN elicits stimulatory immune responses and inhibits tumor growth in grafted mouse models*. J Immunother, 2007. 30(7): p. 715-26.
28. Muir, P. D. and F. W. Gunz, *A cytogenetic study of eight human melanoma cell lines*. Pathology, 1979. 11(4): p. 597-606.
29. Hersey, P., et al., *Adjuvant immunotherapy of patients with high-risk melanoma using vaccinia viral lysates of melanoma: results of a randomized trial*. J Clin Oncol, 2002. 20(20): p. 4181-90.
30. Hersey, P., et al., *Prognostic significance of leukocyte-dependent antibody activity in melanoma patients*. J Natl Cancer Inst, 1983. 71(1): p. 45-53.
31. Hersey, P., et al., *Phase II study of vaccinia melanoma cell lysates (VMCL) as adjuvant to surgical treatment of stage II melanoma. II. Effects on cell mediated cytotoxicity and leucocyte dependent antibody activity: immunological effects of VMCL in melanoma patients*. Cancer Immunol Immunother, 1986. 22(3): p. 221-31.
32. Hersey, P., et al., *Evidence that treatment with vaccinia melanoma cell lysates (VMCL) may improve survival of patients with stage II melanoma. Treatment of stage II melanoma with viral lysates*. Cancer Immunol Immunother, 1987. 25(3): p. 257-65.
33. Altin, J. G., et al., *Synthesis of NTA3-DTDA â€ A Chelator-Lipid that Promotes Stable Binding of His-Tagged Proteins to Membranes*. Australian Journal of Chemistry, 2006. 59(5): p. 302-306.
34. van Broekhoven, C. L., et al., *Engrafting costimulator molecules onto tumor cell surfaces with chelator lipids: a potentially convenient approach in cancer vaccine development*. J Immunol, 2000. 164(5): p. 2433-43.
35. Van Broekhoven, C. L. and J. G. Altin, *A novel system for convenient detection of low-affinity receptor-ligand interactions: chelator-lipid liposomes engrafted with recombinant CD4 bind to cells expressing MHC class II*. Immunol Cell Biol, 2001. 79(3): p. 274-84.
36. van Broekhoven, C. L. and J. G. Altin, *A novel approach for modifying tumor cell-derived plasma membrane vesicles to contain encapsulated IL-2 and engrafted costimulatory molecules for use in tumor immunotherapy*. Int J Cancer, 2002. 98(1): p. 63-72.
37. van Broekhoven, C. L., et al., *Targeting dendritic cells with antigen-containing liposomes: a highly effective procedure for induction of antitumor immunity and for tumor immunotherapy*. Cancer Res, 2004. 64(12): p. 4357-65.
38. van Broekhoven, C. L. and J. G. Altin, *The novel chelator lipid 3(nitrilotriacetic acid)-ditetradecylamine (NTA(3)-DTDA) promotes stable binding of His-tagged proteins to liposomal membranes: potent anti-tumor responses induced by simultaneously targeting antigen, cytokine and costimulatory signals to T cells*. Biochim Biophys Acta, 2005. 1716(2): p. 104-16.
39. U.S. Department of Health and Human Services, *Report on Carcinogens* 2008.
40. Sciences, N. A. o., *Dietary Reference Intake for Vitamin A, Vitamin K, Arsenic, Boron, Chromium, Copper, Iodine, Iron, Manganese, Molybdenum, Nickel, Silicon, Vanadium, and Zinc*. 2000, Washington: National Academy Press.
41. Sunderman, F. W., Jr., *Potential toxicity from nickel contamination of intravenous fluids*. Ann Clin Lab Sci, 1983. 13(1): p. 1-4.
42. Baribaud, F., et al., *Functional and antigenic characterization of human, rhesus macaque, pigtailed macaque, and murine DC-SIGN*. J Virol, 2001. 75(21): p. 10281-.
43. Jameson, B., et al., *Expression of DC-SIGN by dendritic cells of intestinal and genital mucosae in humans and rhesus macaques*. J Virol, 2002. 76(4): p. 1866-75.

What is claimed is:

1. A composition comprising:
   a) one or more antigens;
   b) an anti-DC-SIGN immunoglobulin single variable domain; and
   c) a carrier which carries the one or more antigens and the anti-DC-SIGN immunoglobulin single variable domain;
   wherein the anti-DC-SIGN immunoglobulin single variable domain comprises SEQ ID NO: 1.

2. The composition according to claim 1 further comprising
   d) an immunomodulatory factor.

3. The composition according to claim 2 wherein the immunomodulatory factor is the cytokine interferon gamma.

4. The composition according to claim 1 wherein a) one or more antigen is derived from membrane vesicles.

5. The composition according to claim 4 wherein the membrane vesicles are derived from tumour cells, melanoma cells, or MM200 melanoma cells.

6. The composition according to claim 4 wherein the membrane vesicles comprise membrane-associated antigens.

7. The composition according to claim 6 wherein the membrane-associated antigens are tumour antigens.

8. The composition according to claim 7 wherein the membrane-associated antigens comprise a tumour antigen selected from the group consisting of a melanoma differentiation antigens, tyrosinase, gp100, MART-1, MAGE-A3, MAGE A-10, BAGE, GAGE and XAGE.

9. The composition according to claim 1 wherein the anti-DC-SIGN immunoglobulin single variable domain further comprises a polyhistidine C-terminal tail.

10. The composition according to claim 1 wherein the carrier is a liposome.

11. The composition according to claim 10 wherein the liposome comprises liposomal constituents.

12. The composition according to claim 11 wherein the liposomal constituents comprise the chelator lipid 3(nitrilotriacetic acid)-ditetradecylamine.

13. The composition according to claim 1 wherein the composition is a vaccine composition.

14. The composition according to claim 1 for use as a medicament.

15. The composition according to claim 14 for intravenous administration.

16. The composition according to claim 1 for use in the treatment of cancer.

17. The composition according to claim 16 wherein the cancer is melanoma.

* * * * *